(12) United States Patent
Takeoka et al.

(10) Patent No.: US 8,647,613 B2
(45) Date of Patent: Feb. 11, 2014

(54) DRUG CARRIER

(75) Inventors: Shinji Takeoka, Tokyo (JP); Yosuke Okamura, Tokyo (JP); Hideo Kanazawa, Tokyo (JP); Shuji Hisamoto, Tokyo (JP); Kohei Kubota, Tokyo (JP); Yosuke Obata, Tokyo (JP)

(73) Assignees: JCR Pharmaceuticals Co., Ltd., Ashiya (JP); Waseda University, Tokyo (JP)

( * ) Notice: Subject to any disclaimer, the term of this patent is extended or adjusted under 35 U.S.C. 154(b) by 1420 days.

(21) Appl. No.: 11/886,319

(22) PCT Filed: Mar. 10, 2006

(86) PCT No.: PCT/JP2006/305304
§ 371 (c)(1),
(2), (4) Date: Nov. 29, 2007

(87) PCT Pub. No.: WO2006/098415
PCT Pub. Date: Sep. 21, 2006

(65) Prior Publication Data
US 2009/0136443 A1 May 28, 2009

(30) Foreign Application Priority Data

Mar. 16, 2005 (JP) .................................. 2005-075663
Aug. 31, 2005 (JP) .................................. 2005-252366

(51) Int. Cl.
*A61K 31/787* (2006.01)
(52) U.S. Cl.
USPC .................. 424/78.27; 525/440.04; 525/54.1; 525/54.2
(58) Field of Classification Search
None
See application file for complete search history.

(56) References Cited

U.S. PATENT DOCUMENTS

| | | | | |
|---|---|---|---|---|
| 5,356,633 | A * | 10/1994 | Woodle et al. | 424/450 |
| 2002/0120096 | A1 * | 8/2002 | Tsuchida et al. | 528/332 |
| 2004/0162261 | A1 * | 8/2004 | Tsuchida et al. | 514/44 |
| 2004/0258745 | A1 | 12/2004 | Kai et al. | |
| 2006/0039962 | A1 * | 2/2006 | Heldman et al. | 424/450 |

FOREIGN PATENT DOCUMENTS

| | | |
|---|---|---|
| EP | 160266 A2 | 11/1985 |
| EP | 1219659 A1 | 7/2002 |
| EP | 1420010 A1 | 5/2004 |
| EP | 1 466 649 A1 | 10/2004 |
| JP | 60-231609 A | 11/1985 |
| JP | 2001-64383 A | 3/2001 |
| JP | 2003-64037 A | 3/2003 |
| JP | 2004-307404 A | 11/2004 |

OTHER PUBLICATIONS

Silvius, J. R. et al., Biochemistry, 1993, vol. 32, No. 12, pp. 3153-3161.

* cited by examiner

*Primary Examiner* — Suzanne Ziska
(74) *Attorney, Agent, or Firm* — Birch, Stewart, Kolasch & Birch, LLP

(57) ABSTRACT

The present invention has an object of providing a drug carrier capable of controlling in vivo pharmacokinetics. The present invention is directed to a drug carrier comprising a molecular assembly having a drug incorporated therein, and the above object can be achieved by a part of the amphiphilic molecules included in the molecular assembly being released from the molecular assembly by an external environmental change. The present invention utilizes a phenomenon that the hydrophilic-hydrophobic balance of the amphiphilic molecules is shifted toward hydrophilicity by an external environmental change and thus the amphiphilic molecules are freed from the molecular assembly.

3 Claims, 11 Drawing Sheets (d)

DRUG CARRIER

TECHNICAL FIELD

The present invention relates to a drug carrier preparation comprising a molecular assembly for carrying a drug and controlling pharmacokinetics utilizing a phenomenon that amphiphilic molecules, which form a part of components of the molecular assembly, are released from the molecular assembly.

BACKGROUND ART

Currently, attempts to use a drug carrier having a drug incorporated in a molecular assembly as a drug delivery system are actively studied, and some have already been used in clinical applications. For example, for carrying a hydrophilic drug, there has been proposed a drug carrier encapsulating such a drug in an inner aqueous phase of a bilayer vesicle formed of an assembly of phospholipid molecules, namely, a so-called liposome. For carrying a hydrophobic drug, there has been proposed a drug carrier having such a drug as being physically dissolved or chemically bound to a hydrophobic part of a molecular assembly such as, for example, a lipid microsphere which is an o/w emulsion or a micelle formed of surfactants or amphiphilic polymers. Alternatively, a hydrophobic drug may be encapsulated in a bilayer hydrophobic part of a liposome.

When such a drug carrier is administered to, for example, blood, the drug carrier is mainly taken into macrophage of organisms having a developed reticuloendothelial system (for example, spleen, liver, etc.). Therefore, the residence time of the drug carrier in blood is remarkably short. Such a drug carrier is only used when the target is such an organ. Hence, measures are taken for extending the residence time in blood. For example, a liposome modified with polyethylene glycol chains, that are water-soluble and highly biocompatible polymer, or the like is often used as a so-called Stealth liposome. This technique started by Abuchowski et al. as a study of modifying serum albumin with a polyethylene glycol chain. Already in the first half of the 1990's, adenosine deaminase and asparaginase each modified with a polyethylene glycol chain were approved for clinical use. It has been reported that modification of protein with polyethylene glycol chains provides the effects of, for example, decreasing antigenicity and increasing the ease of residing in blood.

A liposome surface-modified with a polyethylene glycol chain (PEG-liposome) can avoid being taken into a reticuloendothelial system and can reside in blood for an extended period of time. Passive targeting to a solid cancer tissue utilizing this feature is one strategy of drug delivery system.

In general, a solid cancer tissue has features that highly branched neovascularized vessels are abnormally developed and the blood vessel walls are thin and discontinuous. When size of a PEG-liposome, which can reside in blood for a long time, was 300 nm or less, it can leak out from the blood into the stroma through a highly transmissive blood vessel wall in cancer tissue. Once leaked outside, the PEG-liposome is unlikely to return toward the lumen and is accumulated. Therefore, the PEG liposome has an effect of providing the higher integration ability to a solid cancer tissue than a drug of a lower molecular weight, i.e., an EPR effect. Thus, the PEG liposome is one important element in targeting the cancer tissues.

Recently, it has been attempted to cause a surface of a liposome to carry an antibody specifically recognizing a tissue or an organ, a part of an integrin, or a ligand molecule and targeting a tissue or an organ with active recognition. This is called active targeting. In the case of a liposome surface-modified with a polyethylene glycol chain for the purpose of extending the residence time in blood, active targeting is inhibited if the recognition site is concealed by the polyethylene glycol chain. Therefore, a recognition site is bound to a part of a terminus of the polyethylene glycol chain.

From the viewpoint of another aspect of the liposome, i.e., stability, the liposome, which is a molecular assembly, is in a metastable state physicochemically. The reason is that the liposome is prepared utilizing a phenomenon that amphiphilic molecules as a component of the liposome self-assembled by a hydrophobic interaction when being dispersed in water by some type of energy radiation. Therefore, the liposome may aggregate or fuse during storage, which may result in precipitation. In order to solve this, negative-charged lipid or cholesterol is mixed with lipids in a liposome in consideration of the stability in blood, and the surface of the liposome is modified with a polyethylene glycol chain or a glycochain. Therefore, the method of modifying the surface of the liposome with a polyethylene glycol chain is important. A lipid having a polyethylene glycol chain bound to diacylphosphatidylethanolamine or cholesterol is widely used. It has been reported that such a disacyl-type lipid having a polyethylene glycol chain bound thereto is released from a phospholipid bilayer vesicle (J. R. Silvius and M. J. Zuckermann, Biochemistry, 32, 3153, 1993; K. Sou, et al., Bioconjugate, 11, 372, 2000). The release rate of this lipid depends on the molecular weight of the polyethylene glycol chain and the size of the hydrophobic part (the number of carbons forming the acyl chain), i.e., the hydrophilic-hydrophobic balance. A lipid having a relatively large hydrophilic part is easier to be released. The present inventors developed a lipid including one polyethylene glycol chain and a great number of alkyl chains bound to each other using a monodendron structure, and obtained a series of amphiphilic molecules which are not easily released even when a polyethylene glycol chain having a large molecular weight is bound thereto (Japanese Patent No. 3181276).

DISCLOSURE OF THE INVENTION

In the above-described background study, the present inventors clarified that when a series of polyethylene glycol-bound lipids which have been so far synthesized obtains a hydrophilic recognition site, for example, protein, bound to a terminus of a polyethylene glycol chain, such a recognition site is released because the hydrophilicity-hydrophobicity balance is shifted toward hydrophilicity. In order to allow the recognition site to be stably bound to the surface of the liposome so that the hydrophilic recognition site is not released, the present inventors have studied enlarging the hydrophobic part of the lipid to which the recognition site is bound. However, the release still occurred, and it was difficult to completely prevent the release. It seemed that in order to design a molecule for completely preventing the release, a molecular structure having peptide chains extended throughout the membrane a plurality of times, such as transmembrane protein, was necessary. The present inventors newly conceived that control on the release rate would lead to control on the ease of residing in blood of a liposome or control on the sustained-releasability of a drug, instead of considering that the release phenomenon of the lipid having protein-bound polyethylene glycol chain is undesirable. Based on this new conception, the present inventors considered switching the research policy and studied active use of the release phenomenon.

The present inventors set, as one object to be achieved by the present invention, to provide a drug carrier preparation, in which a molecular assembly including amphiphilic molecules support a drug, and which controls in vivo pharmacokinetics of the drug carrier utilizing a phenomenon that a lipid included in the molecular assembly (for example, a polyethylene glycol-bound lipid) is released. The present inventors also found that if the release is accelerated by various external stimulations such as an effect of dilution (concentration change), a temperature change, a pH change, a chemical reaction and the like, this is usable as a method for actively controlling the in vivo kinetics of the drug carrier. The present inventors also set this as an object. The present inventors also studied applying this object to the entire drug carriers based on a molecular assembly such as an emulsion or micelle, as well as a liposome as an assembly of phospholipid molecules.

As a result of active studies to achieve the above-mentioned objects, the present inventors found that by forming amphiphilic molecules included in a molecular assembly of a predetermined molecular structure and thus to changing external environment of the molecular assembly, the release of the amphiphilic molecules can be optionally adjusted; and completed the present invention.

The present invention is directed to a drug carrier comprising a molecular assembly having a drug incorporated therein, wherein in vivo pharmacokinetics are controlled by a part of amphiphilic molecules included in the molecular assembly being released from the molecular assembly by an external environmental change. More specifically, the present invention provides the following drug carrier and the like.

(1) A drug carrier comprising a molecular assembly having a drug incorporated therein, wherein in vivo pharmacokinetics are controlled by a part of amphiphilic molecules included in the molecular assembly being released from the molecular assembly by an external environmental change.

(2) The drug carrier according to (1), wherein the releasable amphiphilic molecules are represented by:

(drug)-(binding site A)-(hydrophilic part)-(binding site B)-(hydrophobic part) . . . 1 or (hydrophilic part)-(binding site B)-(hydrophobic part)-(binding site C)-(drug) . . . 2 wherein, the binding site A is a site for binding the hydrophilic part and the drug, the binding site B is a site for binding the hydrophilic part and the hydrophobic part, and the binding site C is a site for binding the hydrophobic part and the drug.

(3) The drug carrier according to (1), wherein the releasable amphiphilic molecules are represented by:

(hydrophilic polymer)-(binding site D)-(hydrophilic part)-(binding site B)-(hydrophobic part) . . . 3 or (recognition site)-(binding site E)-(hydrophilic polymer)-(binding site D)-(hydrophilic part)-(binding site B)-(hydrophobic part) . . . 4 wherein, the binding site B is a site for binding the hydrophilic part and the hydrophobic part, the binding site D is a site for binding the hydrophilic polymer and the hydrophilic part, and the binding site E is a site for binding the recognition site and the hydrophilic polymer; and the in vivo pharmacokinetics are controlled by the amphiphilic molecules being released.

(4) The drug carrier according to (1), wherein:

an amphiphilic molecule 5 represented by:

(recognition site)-(binding site E)-(hydrophilic part)-(binding site B)-(hydrophobic part) . . . 5 wherein the binding site B is a site for binding the hydrophilic part and the hydrophobic part, and the binding site E is a site for binding the recognition site and the hydrophilic part is incorporated in the molecular assembly;

an amphiphilic molecule 3 represented by:

(hydrophilic polymer)-(binding site D)-(hydrophilic part)-(binding site B)-(hydrophobic part) . . . 3 wherein, the binding site B is a site for binding the hydrophilic part and the hydrophobic part, and the binding site D is a site for binding the hydrophilic polymer and the hydrophilic part is introduced to the molecular assembly and in the state of inhibiting the recognition of the amphiphilic molecule 5; and the in vivo pharmacokinetics are controlled by the amphiphilic molecule 3 being released and thus the recognizing ability of the amphiphilic molecule 5 being appeared.

(5) The drug carrier according to any one of (1) through (4), wherein the hydrophobic part of the releasable amphiphilic molecules includes 2 or greater and 18 or less hydrocarbon chains.

(6) The drug carrier according to (5), wherein the binding site B of the releasable amphiphilic molecules includes an oligosaccharide chain, an oligopeptide chain, a polyester chain, a vinyl-based oligomer or a dendron structure.

(7) The drug carrier according to (1), wherein the releasable amphiphilic molecules are represented by:

(drug)-(binding site A)-(hydrophilic part)-(binding site B)-(hydrophobic part)-(binding site B)-(hydrophilic part) . . . 6 or (drug)-(binding site A)-(hydrophilic part)-(binding site B)-(hydrophobic part)-(binding site B)-(hydrophilic part)-(binding site A)-(drug) . . . 7 wherein, the binding site A is a site for binding the drug and the hydrophilic part, and the binding site B is a site for binding the hydrophilic part and the hydrophobic part].

(8) The drug carrier according to (1), wherein the releasable amphiphilic molecules are represented by:

(hydrophilic polymer)-(binding site D)-(hydrophilic part)-(binding site B)-(hydrophobic part)-(binding site B)-(hydrophilic part) . . . 8, (hydrophilic polymer)-(binding site D)-(hydrophilic part)-(binding site B)-(hydrophobic part)-(binding site B)-(hydrophilic part)-(binding site D)-(hydrophilic polymer) . . . 9, (recognition site)-(binding site E)-(hydrophilic polymer)-(binding site D)-(hydrophilic part)-(binding site B)-(hydrophobic part)-(binding site B)-(hydrophilic part)-(binding site D)-(hydrophilic polymer) . . . 10, or (recognition site)-(binding site E)-(hydrophilic polymer)-(binding site D)-(hydrophilic part)-(binding site B)-(hydrophobic part)-(binding site B)-(hydrophilic part)-(binding site D)-(hydrophilic polymer)-(binding site E)-(recognition site) . . . 11, wherein, the binding site B is a site for binding the hydrophilic part and the hydrophobic part, the binding site D is a site for binding the hydrophilic polymer and the hydrophilic part, and the binding site E is a site for binding the recognition site and the hydrophilic polymer, and the in vivo pharmacokinetics are controlled by the amphiphilic molecules being released.

(9) The drug carrier according to any one of (1) through (8), wherein the hydrophilic part or the hydrophilic polymer of the releasable amphiphilic molecules includes polyethylene glycol.

(10) The drug carrier according to any one of (1) through (9), wherein the amphiphilic molecules are released from the molecular assembly by a dispersion of the molecular assembly being diluted.

(11) The drug carrier according to any one of (1) through (10), wherein the amphiphilic molecules are released from the molecular assembly by a temperature change.

(12) The drug carrier according to any one of (1) through (11), wherein the amphiphilic molecules are released from the molecular assembly by a concentration change of at least one selected from the group consisting of proton, alkaline metal ion and alkaline-earth metal ion.

(13) The drug carrier according to any one of (1) through (12), wherein the releasable amphiphilic molecules include at least one type of bond selected from the group consisting of an ester bond, an amide bond, a urethane bond and a Schiff base in a site for binding the hydrophilic part and the hydrophobic part or in the hydrophobic part, and the amphiphilic molecules are released from the molecular assembly by hydrolysis of such a bond.

(14) The drug carrier according to any one of (1) through (13), wherein the releasable amphiphilic molecules include a disulfide bond in a site for binding the hydrophilic part and the hydrophobic part or in the hydrophobic part, and the amphiphilic molecules are released from the molecular assembly by reduction of the disulfide bond.

(15) The drug carrier according to any one of (1) through (14), wherein the drug incorporated in the molecular assembly is released by partial or entire destruction of a structure of the molecular assembly occurring due to the release of the amphiphilic molecules.

(16) The drug carrier according to any one of (1) through (15), wherein the molecular assembly has a structure of a vesicle.

(17) The drug carrier according to (16), wherein the drug retained in an aqueous phase of the vesicle is released by partial or entire destruction of the structure of the vesicle occurring due to the release of the amphiphilic molecules.

The present invention provides a drug carrier capable of controlling in vivo pharmacokinetics of the drug to be carried in accordance with the purpose thereof.

BEST MODE FOR CARRYING OUT THE INVENTION

Figure 1A:
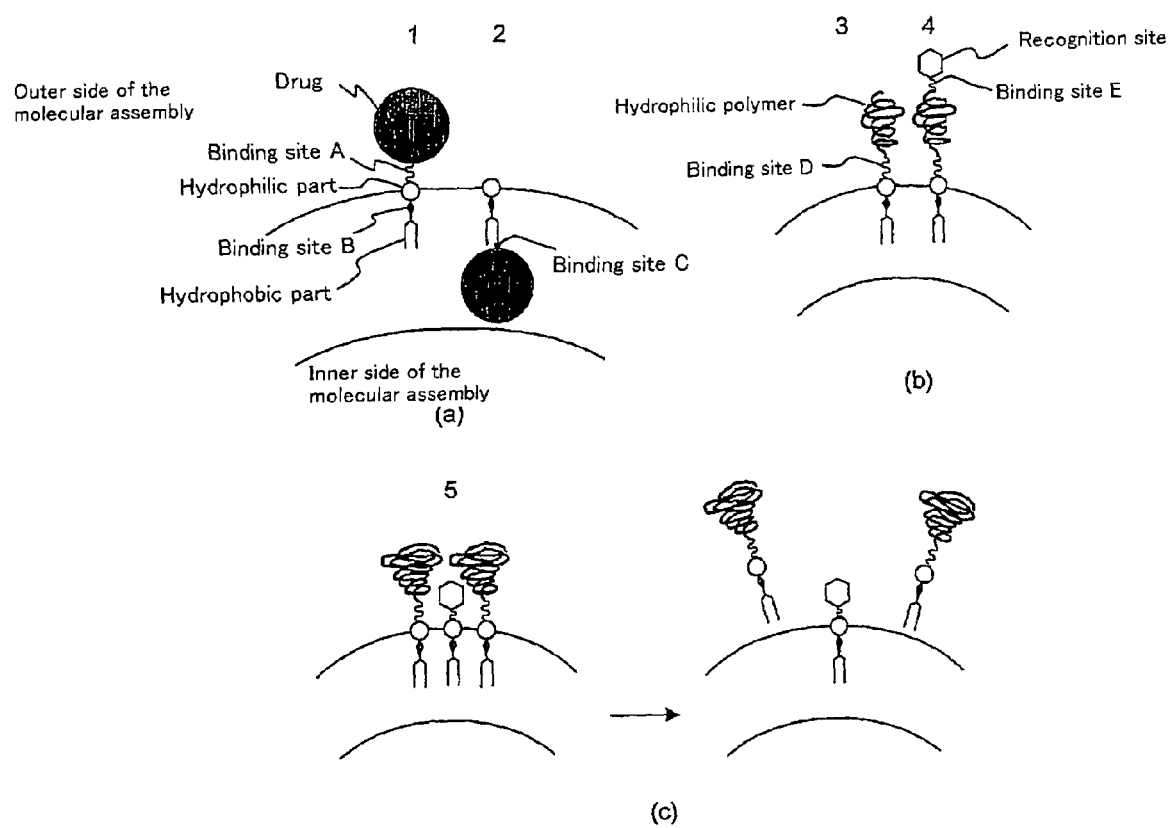
FIG. 1A shows model structures of an amphiphilic molecule usable for a drug carrier according to the present invention.

According to the knowledge from the research based on molecular assembly science by the present inventors, all molecules included in the molecular assemblies are in an equilibrium state between the assembly and solution. In the case of phospholipid, the equilibrium state is significantly shifted toward the assembly. By contrast, a polyethylene glycol-bound lipid which is highly hydrophilic, a single-chain fatty acid which is low in hydrophobicity, a lyso form of phospholipid or the like is in an equilibrium state where many molecules are released in the aqueous phase. The phenomenon that the release behavior of amphiphilic molecules is controlled by the hydrophilic-hydrophobic balance thereof is understood in view of the equilibrium. For example, in an aqueous dispersion of a molecular assembly in a concentrated state, the balance of amphiphilic molecules to be released is shifted toward the assembly. When this aqueous dispersion is diluted, the balance is shifted toward the aqueous, free state. Thus, the amphiphilic molecules to be released are released, and the dispersion reaches a new equilibrium state. The equilibrium is a function of temperature. Therefore, when the temperature is raised, the amphiphilic molecules are released, and the dispersion reaches a new equilibrium state. Release is controlled by such a physical factor. Chemically, release is accelerated as follows. A hydrophobic part or a site for binding the hydrophobic part and a hydrophilic part of the amphiphilic molecules is chemically cleaved to decrease the size of the hydrophobic part. As a result, the hydrophilic-hydrophobic balance is shifted toward hydrophilicity, and thus the release is accelerated. The chemical bond to be cleaved may be a hydrolytic ester bond, an amide bond, a urethane bond, a Schiff base or the like, or a disulfide bond cleaved by a reductant.

Specifically, the present inventors started molecule design in the following circumstances. For amphiphilic molecules capable of adjusting the hydrophilic-hydrophobic balance, a polyethylene glycol-type lipid having a large hydrophilic part was necessary; for example, a lipid including polyethylene glycol covalently bound to an amino group of diacylphosphatidylethanolamine, a lipid including polyethylene glycol covalently bound to a hydroxyl group of a diacyl derivative of glycerol, a lipid including polyethylene glycol covalently bound to a carboxylic group or an amino group of a dialkyl derivative of a trifunctional amino acid (glutamic acid or lysine), or the like. In order to fix stably such a large hydrophilic part on a bilayer, a large hydrophobic part was necessary. As a result, the prevent inventors invented a multi-acyl-type lipid (Japanese Patent No. 3181276). The present inventors used such amphiphilic molecules to analyze the influence of the hydrophilic-hydrophobic balance on the release rate of the amphiphilic molecules, and accumulated much knowledge, on which the present invention is based, regarding the fixation and release of the amphiphilic molecules having a large hydrophobic part on and from a liposome. The present inventors then systematized physical factors and chemical factors on the acceleration of the release.

Instead of attempting to fix polyethylene glycol-type lipid, the present inventors oppositely conceived that the in vivo pharmacokinetics can be effectively controlled in accordance with external stimulations by the release of the lipid.

Hereinafter, a drug carrier according to the present invention will be described more specifically.

First, a molecular assembly usable for a drug carrier according to the present invention will be described. There is no specific limitation on the molecular assembly usable for a drug carrier according to the present invention as long as the molecular assembly can incorporate a drug. Examples of materials usable as such a molecular assembly include polymer assembly, polymer micelle, emulsion, lipid microsphere, bilayer vesicle (liposome), and other molecular assemblies (tube, fiber, ribbon, sheet and the like). Such a molecular assembly includes amphiphilic molecules which can be released from the molecular assembly by an external environmental change and a polymer having a property of forming a molecular assembly with the releasable amphiphilic molecules. There is no specific limitation on the polymer for forming a molecular assembly as long as the polymer has a property of forming a molecular assembly with the releasable amphiphilic molecules, and a synthetic or natural polymer is usable. Examples of such a synthetic polymer include comb-type polymer having a hydrophobic substituent in a hydrophilic main chain such as amphiphilic block copolymer or polysaccharide, and amphiphilic membrane protein. The shape of the polymer assembly formed of such a polymer is typically polymeric micelle, but may be vesicle, fiber, tube, sheet or the like. Alternatively, a aggregate formed of a temperature-responsive vinyl-based polymer such as poly[N-2(hydroxypropyl)methacrylamide] (PHPMA), poly[N-(isopropyl)acrylamide] (PNIPAM) or the like at a temperature equal to or higher than the transition temperature may be used as a component of the molecular assembly.

O/w emulsion or lipid microsphere, in which an oil drop insoluble to water such as triglyceride or the like is stabilized with, for example, a surfactant such as phospholipid, is often used for stably dispersing an oil-soluble drug. In this case, there is no specific limitation on the usable drug, but, for example, doxorubicin derivative, paclitaxel, methotrexate or the like is usable.

A phospholipid vesicle or a liposome used as a multi-purpose drug carrier is a molecular assembly of a vesicle structure having a membrane formed by an intermolecular interaction (hydrophobic interaction, electrostatic interaction, hydrogen bond, or the like) of a lipid and/or a lipoprotein in an aqueous medium, without a covalent bond. The membrane has a single layer (one bilayer) structure or a multi-layer (lamella) structure. The size of the molecular assembly ranges from several tens of nanometers to several tens of micrometers, and is preferably 10 nanometers to 1 micrometer, and more preferably 30 nanometers to 300 nanometers. There are other forms of assembly including bilayer sheet, ribbon, tube, fiber and the like, which are also encompassed in the molecular assembly according to the present invention.

A molecular assembly having a vesicle structure is preferable because such a molecular assembly can retain a water-soluble or oil-soluble drug in an inner aqueous phase or a bilayer of the vesicle and thus can extend the residence time of the drug in blood. Among the molecular assemblies having a vesicle structure, a phospholipid vesicle or a liposome is especially preferable.

A phospholipid vesicle or a liposome is now being actively developed to be used in the field of drug carriers, and includes a single type of phospholipid or a mixture of phospholipid and cholesterol and/or fatty acid.

Examples of the phospholipid include egg yolk lecithin, soybean lecithin, hydrogenated egg yolk lecithin, hydrogenated soybean lecithin, diacylphosphaditylcholin, diacylphosphaditylethanolamine, sphingomyelin, many types of glycolipids and the like. These lipids may include an unsaturated part such as ene (double bond), in (triple bond), diene, diin, triene or the like, or may include a polymerizable group such as vinyl group, for example, styryl group. Specific examples of the polymerizable phospholipid include 1,2-di(octadeca-trans-2,trans-4-dienoyl) phosphatidylcholine, 1,2-di(octadeca-2,4-dienoyl) phosphatidic acid 1,2-biseleostearoyl phosphatidylcholine and the like. The content of the phospholipid is preferably 5 to 70 mol %, and more preferably 20 to 50 mol %, based on the total moles of the lipids included in the molecular assembly.

As a fatty acid included in the acyl chain, a saturated or unsaturated fatty acid having a carbon number of 12 to 20 is used. Examples of such a fatty acid include myristic acid, palmitic acid, stearic acid, oleic acid, linoleic acid, linolenic acid, octadeca-2,4-dienoic acid and the like. Instead of a material having a glycerol backbone, amino acid-type lipids such as trifunctional amino acid, for example, zwitterionic amino acid-type lipids having, for example, glutamic acid or lysine structure are also usable. The content of the fatty acid is preferably 1 to 70 mol %, and more preferably 5 to 30 mol %, based on the total moles of the lipids included in the molecular assembly.

To the molecular assembly, a negative-charged lipid may be added as a component. By mixing the negative-charged lipid in the membrane, the vesicle-to-vesicle aggregation is suppressed, and the number of covered layers is decreased as the result, encapsulation efficiency increase. Examples of the negative-charged lipid include diacylphosphatidylglycerol, diacylphosphatidynic acid, diacylphosphatidylinositol, diacylphosphatidylserine, anionic amino acid-type lipid and the like. The content of the negative-charged lipid is preferably 1 to 70 mol %, and more preferably 5 to 30 mol %, based on the total moles of the lipids included in the molecular assembly.

To the molecular assembly, a sterol usable as a stabilizer may be added as a membrane component of the lipid vesicle as a stabilizer. Examples of such a sterol include all the steroids having perhydrocyclopentanophenanthrene such as ergosterol, cholesterol and the like. Cholesterol is preferable. There is no specific limitation on the content of the sterol. In consideration of the stability of the vesicle, the content of the sterol is preferably 5 to 50 mol %, and more preferably 15 to 40 mol %, based on the total moles of the lipids included in the molecular assembly.

According to the present invention, the molecular assembly includes amphiphilic molecules which can be released from the molecular assembly by an external environmental change. The content of the amphiphilic molecules is appropriately determined in accordance with the type of organ or tissue as a target, the type of drug, the site where the drug is included, the method for inclusion of the drug, the form of the molecular assembly and the like, and is not specifically limited to any value. For example, the content of the amphiphilic molecules is preferably 0.01 to 100 mol %, more preferably 0.05 to 50 mol %, and especially preferably 0.1 to 30 mol %, based on the total moles of the lipids included in the molecular assembly.

There is no specific limitation on the method for preparation of the molecular assembly, and any generally known method is usable. For example, a liposome may be prepared as follows. Powder or thin film of a single type of lipid or a mixture of lipids is hydrated and dispersed, and then the liposome is prepared by a high pressure extrusion method, an ultrasonic radiation method, a stirring (vortex mixing, homogenizer) method, a freeze-thaw method, a microfluidizer method or the like. Alternatively, a single type of lipid or a mixture of lipids is dissolved in an organic solvent, the resultant solution is injected into an aqueous phase, and then the organic solvent such as ethanol, ether or the like is removed in vacuo or by dialysis. Still alternatively, a single type of lipid or a mixture of lipids is dispersed in an aqueous phase together with a surfactant such as sodium cholade, sodium dodecyl sulfate, or a nonionic surfactant such as Triton X, laurylether or the like to form an emulsion, followed by removal of the surfactant by dialysis. Also, a reverse phase vaporization method, an incubation method and the like are usable.

Any of these methods for allowing a molecular assembly to incorporate a drug may be appropriately selected in accordance with the type of drug or the like. In the case of a water-soluble drug, the drug may be dissolved in an aqueous phase at the time of liposome production. Alternatively, after the liposome is prepared, a water-soluble drug may be added to an external aqueous phase and encapsulated in an inner aqueous phase using the permeability of the liposome membrane. An unencapsulated water-soluble drug can be separated from the encapsulating vesicle by gel filtration, ultracentrifugal separation, ultrafiltration or the like. In the case of an oil-soluble drug, for example, the drug may be added in the state where a single type of lipid or a mixture of lipids is dissolved in an organic solvent, and the liposome is produced in the above-described method. Thus, the drug may be incorporated in a hydrophobic part of the bilayer. Alternatively, after a liposome including amphiphilic molecules having a functional group, is formed, the drug may be allowed to be carried by the functional group exposed on the surface of the liposome using a chemical reaction in the aqueous phase. Still alternatively, after the liposome is produced, the drug may be dissolved in an organic solvent miscible with water, and the resultant substance may be added to an external aqueous phase to introduce the drug to a hydrophobic part of the bilayer.

Next, specific embodiments of a drug carrier according to the present invention will be described.

According to the present invention, a phenomenon that a part of amphiphilic molecules included in a molecular assembly is released from the molecular assembly by an external environmental change of the molecular assembly is utilized. A drug carrier according to the present invention controls in vivo pharmacokinetics by this release phenomenon of the amphiphilic molecules. The term "external environment" refers to environment surrounding the molecular assembly, such as the temperature, pH, dilution of the molecular assembly, ionic environment, reducing atmosphere and the like.

The amphiphilic molecules releasable from the molecular assembly are capable of controlling the release rate from the molecular assembly by the hydrophilic-hydrophobic balance therein. The release rate may be appropriately adjusted from the view of the type of organ or tissue as a target, the type of drug, the site where the drug is incorporated, the incorporation method of the drug, the form of the molecular assembly and the like. For example, the release rate can be decreased by designing the amphiphilic molecules such that the ratio of the hydrophobic part with respect to the hydrophilic part is higher. By contrast, the release rate can be increased by designing the amphiphilic molecules such that the ratio of the hydrophilic part with respect to the hydrophobic part is higher.

There is no specific limitation on the drug carrier according to the present invention as long as the drug carrier is capable of controlling the pharmacokinetics by a part of the amphiphilic molecules being released from the molecular assembly. A drug carrier according to the present invention may be provided in, for example, the following four embodiments, which are different in terms of the combination of the hydrophilic part, the hydrophobic part, the drug and the hydrophilic polymer of the releasable amphiphilic molecules, and the control method.

In a first embodiment of the present invention, the pharmacokinetics are controlled by causing the hydrophilic part or the hydrophobic part of the releasable amphiphilic molecules to conjugate a drug (FIG. 1A(a)). In a second embodiment of the present invention, the pharmacokinetics are controlled by causing the hydrophilic part of the releasable amphiphilic molecules to conjugate a hydrophilic polymer or a hydrophilic polymer having a recognition site bound thereto (FIG. 1A(b)). In a third embodiment of the present invention, the pharmacokinetics are controlled by release of the amphiphilic molecules from the molecular assembly and thus emergence of the recognition site on the surface of the carrier such as a liposome or the like (active targeting; FIG. 1A(c)). In a fourth embodiment of the present invention, the pharmacokinetics are controlled by the releasable amphiphilic molecules specifically having a transmembrane structure (FIG. 1B(d)). Hereinafter, each embodiment will be described.

First Embodiment

In a drug carrier according to the first embodiment of the present invention, the releasable amphiphilic molecules include a drug, a hydrophilic part and a hydrophobic part. The pharmacokinetics are controlled by causing the releasable amphiphilic molecules to conjugate a drug (FIG. 1A(a)). The amphiphilic molecules having a drug bound thereto which are released from the molecular assembly in this embodiment (hereinafter, occasionally referred to as "drug-bound amphiphilic molecules") may have a structure of an amphiphilic molecule 1 and an amphiphilic molecule 2.

(drug)-(binding site A)-(hydrophilic part)-(binding site B)-(hydrophobic part) . . . 1

(hydrophilic part)-(binding site B)-(hydrophobic part)-(binding site C)-(drug) . . . 2 wherein, the binding site A is a site for binding the hydrophilic part and the drug, the binding site B is a site for binding the hydrophilic part and the hydrophobic part, and the binding site C is a site for binding the hydrophobic part and the drug.

The portion of (hydrophilic part)-(binding site B)-(hydrophobic part) may be included in all the known amphiphilic molecules such as phospholipid, sphingolipid, amino acid-type lipid and the like. The hydrophilic part may be a usually known hydrophilic part of an amphiphilic molecule, or may include a hydrophilic polymer such as polyethylene glycol, polysaccharide, polyvinyl alcohol, polyvinyl pyrrolidone, polyglutamic acid, polypeptide or the like.

The binding site B is a site for binding the hydrophilic part and the hydrophobic part, and is not limited to any specific material as long as the material is known as usually having such a function. The binding site B is bound with one hydrophilic part and one or two or more hydrophobic parts via an amino acid such as glycerol, oligosaccharides, oligopeptides, polyesters, vinyl-based oligomer, glutamic acid, lysine or the like, or via a multi-branched structure formed thereof, for example, a dendron structure. It is preferable that the binding site B is formed of at least one type selected from the group consisting of oligosaccharide chain, oligopeptide chain, polyester chain, vinyl-based oligomer and a dendron structure among these. For example, an oligopeptide chain formed of repetition of glutamic acid having a glycine unit as a spacer has an optional number of carboxylic acid groups in a side chain thereof. To the carboxylic acid groups, an optional number of hydrophobic parts can be introduced by an amide bond or an ester bond. A hydrophilic part can be bound to an N terminus of the oligopeptide chain. Alternatively, a hydrophobic part can be bound to a carboxylic acid group or a hydroxyl group of oligoacrylic acid or oligovinyl alcohol by polymerization reaction. For example, in the case where such an oligomer is polymerized by iniferter polymerization, the molecular weight can be controlled and a functional group can be introduced to a terminus. Thus, a hydrophilic part can be bound to the terminus. In the case of monodendron formed of glutamic acid or lysine, the number of the functional groups can be controlled in accordance with the generation. The number of the functional groups is 2 for the first generation, 4 for the second generation, and 8 for the third generation. By binding hydrophobic parts thereto, the number of the hydrophobic parts can be controlled. The hydrophilic part can be bound to one functional group which is on the opposite side of the monodendron.

The hydrophobic part is not limited to any specific material as long as the material can provide a sufficient level of hydrophobicity to the amphiphilic molecules. Examples of materials usable for the hydrophobic part include saturated fatty acid, unsaturated fatty acid, saturated higher alcohol, unsaturated higher alcohol, steroids and the like. These materials may be of a straight chain or a branched chain.

According to the present invention, it is preferable that the hydrophobic part of the releasable amphiphilic molecule has two or more hydrocarbon chains. Here, the expression "the hydrophobic part has two or more hydrocarbon chains" means that two or more hydrocarbon chains are bound to the binding site B. The hydrocarbon chain may be a branched chain. Such a branched chain, for example, has an isoprenoid structure in a long chain.

There is no specific limitation on the number of hydrocarbon chains, but two or more is preferable. There is no specific upper limit on the number of hydrocarbon chains, but the number is preferably 18 or less in terms of simplification of synthesis.

A hydrocarbon chain to be introduced to the hydrophobic part is preferably an alkyl chain, an alkenyl chain or an alkynyl chain, and especially preferably an alkyl chain, which minimizes the steric hindrance and can be easily introduced to the molecular assembly. The hydrocarbon chain may have a substituent as long as the hydrocarbon chain has a sufficient level of hydrophobicity as a hydrophobic part of the amphiphilic molecule and does not inhibit introduction of the amphiphilic molecule to the molecular assembly. The hydrocarbon chain may be disconnected by an oxygen atom, a sulfur atom, —NR— (where R is an alkyl group, an alkenyl group or an alkynyl group which may have a substituent) or the like. There is no specific limitation on the number of carbons of the hydrocarbon chain, but the number is preferably 4 to 24, more preferably 10 to 20, and especially preferably 12 to 18. In the case where the binding site B includes glutamic acid or lysine, the above-mentioned hydrophobic part may be bound to two carboxylic groups or two amino groups of glutamic acid or lysine, respectively.

Specifically, materials that can be used as the amphiphilic molecule represented as (hydrophilic part)-(binding site B)-(hydrophobic part) include polyethylene glycol-bound lipid, glycolipid, peptide-bound lipid, protein (antibody, enzyme, etc.)-bound lipid, amphiphilic molecule conjugating drugs such as an nucleic acid or the like, multi-acyl chain-type lipid, transmembrane-type lipid and the like. With respect to polyethylene glycol-bound lipid include polyethylene glycol, and a copolymer of ethylene glycol and propylene glycol, which have a molecular weight of about 200 Da to 12500 Da, preferably about 1000 Da to 5000 Da, and have a substituent such as an amino group, a carboxyl group, a hydroxyl group, a maleimide group or the like at one terminus or both termini. Examples of polyethylene glycol-bound lipid also include derivatives obtained by activating a terminal substituent thereof. Glycolipid may have a reducing terminal, and its oligosaccharide or polysaccharide may be a branched or straight chain, whose glycopolymerization degree is 2 to 400. Glycolipid may be either natural sugar or synthetic sugar. Oligosaccharide is sugar obtained by, for example, α binding or β binding of one type, or two or more types, of glucose, fructose, xylose, galactose, mannose, glucosamine and the like. Examples of oligosaccharide include maltooligosaccharide, laminarioligosaccharide, cellooligosaccharide, isomaltooligosaccharide, gentiooligosaccharide, nigerooligosaccharide, lactooligosaccharide, melioligosaccharide, inulooligosaccharide, and the like. Examples of polysaccharide include starch, cellulose, mucopolysaccharide (hyaluronic acid, chondroitin, chondroitin sulfate, delmantan sulfate, keratan sulfate, heparin, etc.), chitin, chitosan, other decomposition products of polysaccharides, cell, cell-derived composite saccharides and the like.

In this embodiment, the drug is introduced to the molecular assembly through coassembling by the amphiphilic molecule 1 represented by the formula 1 in which the drug is bound to the hydrophilic part via the binding site A or the amphiphilic molecule 2 represented by the formula 2 in which the drug is bound to a terminus of the hydrophobic part via the binding site C. The binding sites A and C are sites for binding the drug to the hydrophilic part and the hydrophobic part, respectively. The binding sites A and C may be each an amide bond, an ester bind, an ether bond, a urethane bond, a disulfide bond, an addition bond of a mercapto group and a maleimide group.

There is no specific limitation on the drug which can be conjugated to the drug carrier according to the present invention as long as the drug acts on one of the target organs or tissues. Examples of such a drug include enzymes, peptides or proteins, various antibiotics, various peptide hormones, DNAs, RNAs, siRNAs, plasmids, various anticancer drugs, drugs for central nervous system, drugs for peripheral nervous system, drugs for sensory organs, drugs for circulatory organs, drugs for respiratory organs, drugs for digestive organs, hormones, drugs for urinary and genital organs and anus, dermatologic drugs, drugs for dental and oral use, vitamins, nutritional supplements, drugs for blood and bodily fluids, drugs for dialysis, other metabolic drugs, drugs for cell activation, drugs for tumors, radioactive drugs, drugs for allergies, drugs based on prescriptions of pharmacognosy and traditional Chinese medicine, antibiotic preparations, drugs for chemical therapy, biological preparations, diagnostic drugs and the like. Examples of peptides and proteins include various cytokines such as interleukin and the like; polypeptides as extracellular matrices such as cell transfer factors, fibrinogen, collagen, keratin, proteoglucan and the like, or oligo forms as a part of the structure of the polypeptides; functional polypeptides such as oxytocin, bradykinin, thyrotrobin releasing factor, enkephalin and the like. Examples of enzymes include catalase, chymotrypsin, cytochrome, amylase and the like. The drugs which can be incorporated in the drug carrier according to the present invention, are not limited to the above-listed drugs. These drugs may be used individually or in a combination of two or more.

When the molecular assembly is administered to, for example, blood, the molecular assembly is diluted and as a result, the drug-bound amphiphilic molecules introduced in the liposome are released. The released drug-bound amphiphilic molecules circulate along the blood flow, and absorbed, metabolized and excreted. The drug-bound amphiphilic molecules are released from the molecular assembly one-handedly without reaching an equilibrium state. An amphiphilic molecule, the hydrophilic-hydrophobic balance of which is more shifted toward hydrophilicity, has a higher release rate. The release rate can be controlled by the molecular weight or charged amount of the hydrophilic polymer in the hydrophilic part, or the length or number of the hydrocarbon chains such as alkyl long chains in the hydrophobic part.

The hydrophilic-hydrophobic balance of the amphiphilic molecule 1 or 2 may be appropriately designed in accordance with the type of drug, the type of organ or tissue as a target, the state of disease, the kinetics of the amphiphilic molecule 1 or 2 itself or the like. The amphiphilic molecule 1 or 2 may be introduced to the bilayer of the molecular assembly, for example, a liposome formed of, for example, phospholipid by the above-described method.

In the first embodiment, the content of the amphiphilic molecule 1 or 2 may be appropriately determined in accordance with the type of drug, the type or organ or tissue as a target, the state of disease or the like, and is preferably 0.01 to 30 mol %, and more preferably 0.1 to 10 mol %, based on the total moles of the lipids included in the molecular assembly.

Second Embodiment

In a drug carrier according to the second embodiment of the present invention, the pharmacokinetics are controlled by causing the hydrophilic part of the releasable amphiphilic molecules bound to a hydrophilic polymer or a hydrophilic polymer having a recognition site bound thereto (FIG. 1A(b)). The drug carrier according to the second embodiment of the present invention includes a "hydrophilic polymer" in place of the "drug" in the first embodiment, and basically includes a hydrophilic polymer, a hydrophilic part and a hydrophobic part. This embodiment encompasses a drug carrier in which the hydrophilic polymer has a recognition site bound thereto.

The amphiphilic molecules which are released from the molecular assembly in this embodiment may have a structure of an amphiphilic molecule 3 and an amphiphilic molecule 4 having a hydrophilic polymer bound thereto.

(hydrophilic polymer)-(binding site D)-(hydrophilic part)-(binding site B)-(hydrophobic part) . . . 3

(recognition site)-(binding site E)-(hydrophilic polymer)-(binding site D)-(hydrophilic part)-(binding site B)-(hydrophobic part) . . . 4 wherein, the binding site B is a site for binding the hydrophilic part and the hydrophobic part, the binding site D is a site for binding the hydrophilic polymer and the hydrophilic part, and the binding site E is a site for binding the recognition site and the hydrophilic polymer.

The amphiphilic molecule represented by the formula 3 or 4, can modify the surface of the liposome with the hydrophilic polymer, by being coassembled with, for example, phospholipids. Examples of usable hydrophilic polymers may be the same as those described regarding the hydrophilic part in the first embodiment. The molecular weight of the hydrophilic polymer is preferably about 200 Da to 20000 Da, and especially preferably about 2000 Da to 12500 Da. If a hydrophilic polymer, which is formed of a polyethylene glycol chain, provides an effect of significantly extending the residence time of the liposome in blood as compared to an unmodified liposome. If the hydrophilic polymer itself is formed of polysaccharide that is easily recognized by certain cells forming an organ or tissue, it can improve the specificity to the organ or tissue. Especially the amphiphilic molecule 4 has a recognition site such as an oligopeptide chain or a glycochain at a terminus of the hydrophilic polymer such as, for example, a surface-modified polyethylene glycol chain, and can control the in vivo kinetics of the drug carrier.

According to the present invention, the in vivo kinetics of the drug carrier can be more precisely controlled by release of the amphiphilic molecule 3 or 4 by an external environmental change. For example, the polyethylene glycol-bound lipid which modifies the liposome extends the residence time of the liposome in blood. The residence time in blood can be shortened by, for example, release of the polyethylene glycol-bound lipid from the liposome. The release rate can be adjusted by the molecular weight of polyethylene glycol or the size of the hydrophobic part. A liposome having the amphiphilic molecule 4 introduced thereto can improve the specific accumulation to the cells, forming the organ or tissue, which recognize the amphiphilic molecule 4. However, if the amphiphilic molecule 4 is released, the specificity is decreased, and it further decreased because they bind to the recognized site of the cells and inhibit recognition of other modified liposome. As a result, the specificity is further decreased. The in vivo kinetics of the drug carrier can be more precisely controlled by mixing the amphiphilic molecules 3 and 4 and introducing the mixture to the surface of the liposome, and then controlling the release rate of each of the amphiphilic molecules 3 and 4.

There is no specific limitation on the binding site D as long as the binding site D is a bond of a hydrophilic polymer and a hydrophilic part. There is no specific limitation on the binding site E as long as the binding site E is a bond of a hydrophilic polymer and a recognition site. The binding mode in sites D and E may be each an amide bond, an ester bind, an ether bond, a urethane bond, a disulfide bond, a condensation bond of a mercapto group and a maleimide group, a Schiff base of an aldehyde group and an amino group, or the like.

There is no specific limitation on the recognition site as long as the recognition site specifically recognizes a certain organ or tissue as a target. Examples of materials usable for the recognition site include oligosaccharide, antibody, peptide hormone, lectin, glycoprotein and the like mentioned above, but the recognition site is not limited to these materials.

In the second embodiment, the content of the amphiphilic molecule 3 or 4 may be appropriately determined in accordance with the desired residence time in blood or recognition ability, and is preferably 0.01 to 50 mol %, and more preferably 0.1 to 20 mol %, based on the total moles of the lipids included in the molecular assembly.

Third Embodiment

In a drug carrier according to the third embodiment of the present invention, the recognition sites on the surface of the molecular assembly are detectable after a part of amphiphilic molecules are released from the molecular assembly, and thus pharmacokinetics can be controlled (FIG. 1A(c)). A drug carrier according to the third embodiment, for example, includes a molecular assembly having an amphiphilic molecule 5 and an amphiphilic molecule 3 which inhibits the recognition of the amphiphilic molecule 5, and controls the pharmacokinetics by the amphiphilic molecule 3 being released and thus the recognition ability of the amphiphilic molecule 5 being displayed.

(recognition site)-(binding site E)-(hydrophilic part)-(binding site B)-(hydrophobic part) . . . 5

(hydrophilic polymer)-(binding site D)-(hydrophilic part)-(binding site B)-(hydrophobic part) . . . 3 wherein, the binding site B and the binding site D are the same as above, and the binding site E is a site for binding the recognition site and the hydrophilic part.

In this embodiment, where the amphiphilic molecule 5 and the amphiphilic molecule 3 are coassembled on the surface of the molecular assembly, it is preferable that the hydrophilic polymer of the amphiphilic molecule 3 has a larger molecular weight than that of the recognition site of the amphiphilic molecule 5. By using the amphiphilic molecules in such a combination, the hydrophilic polymer can inhibit the recognition site on the surface of the molecular assembly from being recognized by the cells in a certain organ or tissue. When the molecular assembly is administered to blood in this state, the amphiphilic molecule 3 is released by an external environmental change such as a dilution effect or the like. When this causes the recognition site of the amphiphilic molecule 5 to be exposed on the surface of the liposome, the recognition site improves the specific integration ability to the cells in the certain organ or tissue. Thus, the in vivo pharmacokinetics of the drug carrier can be controlled. Furthermore, the specific integration ability is decreased when the amphiphilic molecule 5 is released, which can also make it possible to control the in vivo pharmacokinetics of the drug carrier. The materials on the recognition site of the amphiphilic molecule 5 may be the same as described in the second embodiment.

For example, the amphiphilic molecule 5 may have a recognition site such as an oligopeptide chain, a glycochain or the like at a terminus of the hydrophilic part such as glutamic acid, lysine or the like. Especially, the glycochain is structure-specifically recognizable by lectin, which is a sugar binding protein. Therefore, a molecular assembly including the amphiphilic molecule 5 having a glycochain as the recognition site is usable as a carrier which specifically recognizes a ligand or a receptor such as protein or glycochain on the cell surface, and is highly useful.

The amphiphilic molecule 3 may be the molecule described in the second embodiment. In this embodiment, the recognition ability of the amphiphilic molecule 5 is inhibited by the hydrophilic polymer of the amphiphilic molecule 3, such as polyethylene glycol or the like. There is no specific limitation on the hydrophilic polymer of the amphiphilic molecule 3 as long as the hydrophilic polymer can inhibit the recognition ability of the amphiphilic molecule 5. The molecular weight of the hydrophilic polymer is preferably about 200 Da to 20000 Da, and more preferably about 2000 Da to 12500 Da.

In the third embodiment, the content of the amphiphilic molecule 5 may be appropriately determined in accordance with the desired recognition ability, and is preferably 0.01 to 50 mol %, and more preferably 0.1 to 30 mol %, based on the total moles of the lipids included in the molecular assembly. The content of the amphiphilic molecule 3 may be any value in the range at which the recognition ability of the amphiphilic molecule 5 can be inhibited, and is preferably 0.01 to 30 mol %, and more preferably 0.05 to 10 mol %, based on the total moles of the lipids included in the molecular assembly.

The release rate of the amphiphilic molecule 3 can be controlled by the molecular weight or the charge number of the hydrophilic polymer or the size of the hydrophobic part. The release rate of the amphiphilic molecule 5 can also be controlled in the same manner. Accordingly, the relative release rate of these amphiphilic molecules can be appropriately designed in accordance with the purpose.

Fourth Embodiment

Figure 1B:
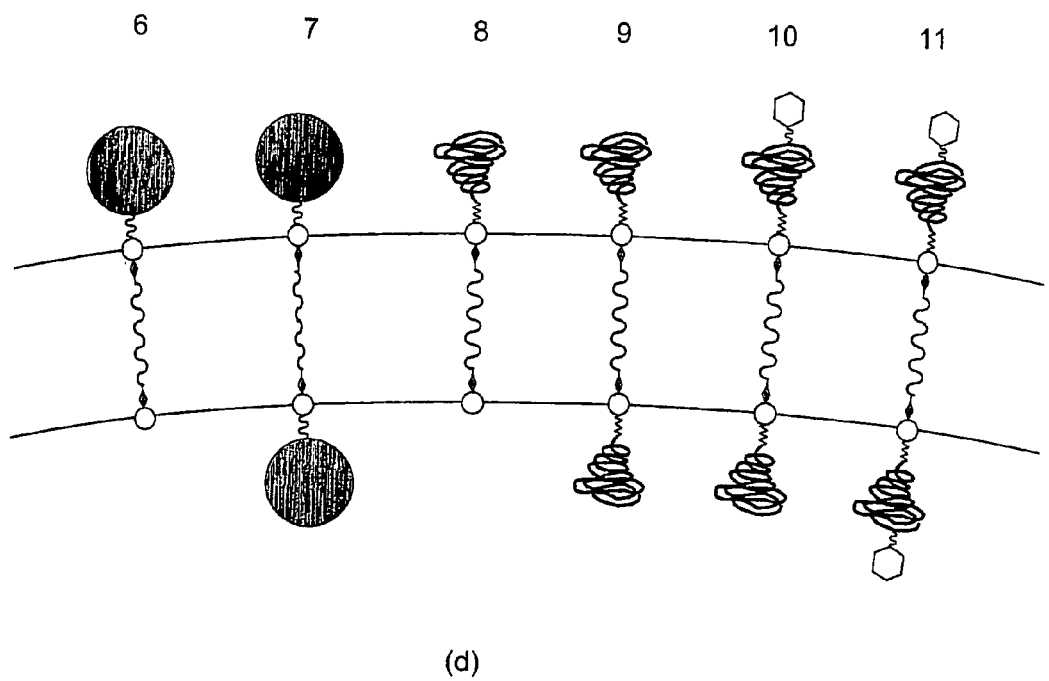
FIG. 1B shows a model structure of an amphiphilic molecule usable for a drug carrier according to the present invention.

In the fourth embodiment of the present invention, the in vivo pharmacokinetics of a drug carrier is controlled by release of transmembrane amphiphilic molecules extendable throughout the membrane of the molecular assembly (FIG. 1B(d)). Simply stating, the releasable amphiphilic molecules illustrated in the first through third embodiments are classified as having a structure represented by (hydrophilic part)-(hydrophobic part). On the other hand, the amphiphilic molecules with the structure of (hydrophilic part)-(hydrophobic part)-(hydrophilic part) are also usable for the present invention. In this embodiment, amphiphilic molecules having such a structure are preferable.

Specific examples of the amphiphilic molecules used in this embodiment are represented by:

(drug)-(binding site A)-(hydrophilic part)-(binding site B)-(hydrophobic part)-(binding site B)-(hydrophilic part) . . . 6, (drug)-(binding site A)-(hydrophilic part)-(binding site B)-(hydrophobic part)-(binding site B)-(hydrophilic part)-(binding site A)-(drug) . . . 7, (hydrophilic polymer)-(binding site D)-(hydrophilic part)-(binding site B)-(hydrophobic part)-(binding site B)-(hydrophilic part) . . . 8, (hydrophilic polymer)-(binding site D)-(hydrophilic part)-(binding site B)-(hydrophobic part)-(binding site B)-(hydrophilic part)-(binding site D)-(hydrophilic polymer) . . . 9, (recognition site)-(binding site E)-(hydrophilic polymer)-(binding site D)-(hydrophilic part)-(binding site B)-(hydrophobic part)-(binding site B)-(hydrophilic part)-(binding site D)-(hydrophilic polymer) . . . 10, or (recognition site)-(binding site E)-(hydrophilic polymer)-(binding site D)-(hydrophilic part)-(binding site B)-(hydrophobic part)-(binding site B)-(hydrophilic part)-(binding site D)-(hydrophilic polymer)-(binding site E)-(recognition site) . . . 11.

wherein, the binding site A, the binding site B, the binding site D, and the binding site E are the same as those as above.

These amphiphilic molecules are introduced to an assembly, for example, while having a structure extendable throughout the bilayer of the liposome. The hydrophobic part may have a single chain, or two or more chains, which is determined by the binding site B. The hydrophobic part may have any length as long as the amphiphilic molecule is extendable throughout the bilayer, and has a carbon number of preferably 20 to 50, more preferably 28 to 36. The symmetric structure of the amphiphilic molecule 7 or 9 is easy to synthesize. When, for example, a liposome is formed, such a structure allows the hydrophilic polymer or drug to be located in the inner aqueous phase side of the liposome. This may be convenient to control the release rate, i.e., to control the pharmacokinetics, whereas it is also possible that the hydrophilic polymer or drug do not function effectively because they are not exposed on the surface of the liposome. In the latter case, after the amphiphilic molecules are introduced to the liposome, the drug or hydrophilic polymer may be bound only to the terminus of the amphiphilic molecules exposed on the surface via the binding site A or D. As to controlling the release rate of the transmembrane amphiphilic molecules, the size and the charge number of the hydrophilic part on the inner aqueous phase are important factors as well as the hydrophilic-hydrophobic balance. Namely, even if though the hydrophobicity of a transmembrane amphiphilic molecule is low, if the hydrophilicity on the inner aqueous phase side is high, the transmembrane amphiphilic molecule is difficult to be released from the liposome.

In the fourth embodiment, there is no specific limitation on the content of the amphiphilic molecules 6 through 11. The content is preferably 0.01 to 100 mol %, especially 0.1 to 25 mol %, based on the total moles of the lipids included in the molecular assembly.

[Method for Controlling the Release Rate of the Amphiphilic Molecules]

The phenomenon that amphiphilic molecules are released from the molecular assembly occurs when external environmental changes. The "external environment" means, as described above, environment surrounding the molecular assembly. The external environmental factors includes, for example, diluent to dilute the molecular assembly, the ambient temperature to change the temperature of the molecular assembly, the ambient proton concentration to change the pH of the molecular assembly, and the like. The external environmental change is not limited to a shift from the equilibrium state to a nonequilibrium state by the dilution occurring when the molecular assembly is administered to blood. The equilibrium state is also shifted by the temperature. For example, when the temperature is raised, the equilibrium state is shifted toward intention of release, and thus the release can be accelerated. The equilibrium state is also influenced by the motility in the molecular assembly. For example, a dipalmitoylphosphatidylcholine liposome has a gel-liquid crystal phase transition temperature of 42° C. Thus, the molecule packing state of the membrane is more disturbed and the release is more likely to occur at 40° C. that is in the vicinity of the phase transition temperature or at 43° C. that is above the phase transition temperature than at 35° C. below the phase transition temperature. Therefore, at such temperatures, the amphiphilic molecules can be locally released from the molecular assembly by local heating by using a portable warmer, infrared, microwave, a catheter or the like. Alternatively, the temperature of the liposome can be locally controlled by encapsulating microparticles of iron oxide in the liposome and heating the liposome with microwave. The phase transition temperature can be changed by changing combination and composition of lipids that have different phase transition temperatures, such as dimyristoylphosphatidylcholine and dipalmitoylphosphatidylcholine. In the case where the hydrophilic polymer of the releasable amphiphilic molecules is a temperature-responsive polymer such as poly-(N-isopropylacrylamide) (PNIPAM) or the like, the hydrophilicity is increased and the release is more likely to occur at a temperature equal to or lower than the phase transition temperature.

The release rate of the amphiphilic molecules from the molecular assembly can be adjusted by changing concentration change of proton, alkaline metal ion, or alkaline-earth metal ion. For example, in the case where the hydrophilic part includes an amino group, the amino group is protonated at a low pH to improve the hydrophilicity and thus the release rate is increased. In the case where the hydrophilic part includes a carboxylic acid group, the carboxylic acid group is dissociated at a high pH to improve the hydrophilicity and thus the release rate is increased.

It is also preferable that the binding site or the hydrophobic part of the releasable amphiphilic molecules includes at least one type of bond selected from the group consisting of an ester bond, an amide bond, a urethane bond and a Schiff base, and the amphiphilic molecules are released from the molecular assembly by the hydrolysis of such a bond. For example, when pH decreases, hydrolysis occurs in an amphiphilic molecule that consists of a lysine at binding site B, a long chain alcohol combined to the carboxyl group by ester bond as a hydrophobic part and a long chain fatty acid combined to the amino group by amide bound as another hydrophobic part; or in an amphiphilic molecule in which the binding site is a dicarboxylic acid derivative such as 2-aminopentanedioic acid, and a hydrophobic part is introduced by binding a long chain alcohol to the carboxylic group thereof by an ester bond; or in an amphiphilic molecule in which a hydrophobic part is introduced by binding a fatty acid to glycerol by an ester bond; hydrolysis occurs by a pH decrease. As a result, the bond is dissociated to significantly shift the hydrophilic-hydrophobic balance of the amphiphilic molecule toward hydrophilicity, and thus the decomposed amphiphilic molecule is released. This release phenomenon significantly disturbs the molecule packing state of the bilayer of the liposome, and the release of the encapsulated drug is accelerated. Thus, the in vivo kinetics of the drug carrier can be controlled. Such in vivo kinetics act on cells as well as the blood flow, organs and tissues. A system of releasing amphiphilic molecules in response to pH change is usable to control intracellular kinetics.

An amphiphilic molecule having a phosphoric acid group in the hydrophilic part is bound to bivalent cation such as calcium ion, and thus the hydrophilic-hydrophobic balance thereof is shifted toward hydrophobicity. As a result, the release rate is decreased, which can be utilized in the present invention. Furthermore, by capturing the calcium ion using a chelate agent such as citric acid or the like, the suppressed release rate can be increased. In general, in amphiphilic molecules having a dissociating group in the hydrophilic part that control the hydrophilic-hydrophobic balance, charge is shielded by an increase of the aqueous phase ion strength. Therefore, the hydrophilic-hydrophobic balance is shifted toward hydrophobicity, and as a result, the release rate is decreased as a result It is also preferable that the binding site B or one hydrophobic part of the releasable amphiphilic molecules includes a disulfide bond, and the amphiphilic molecules are released from the molecular assembly by being cleaved due to the reduction of the disulfide bond. In an example of such amphiphilic molecules, a fatty acid is introduced to an amino group of cysteine by an amino bond, another hydrophobic part is introduced to a mercapto group of cysteine by a disulfide bond of alkanethiol, and a hydrophilic part is introduced to a carboxylic acid group. It is also effective to introduce a disulfide group to an alkyl chain of the hydrophobic part, such as the transmembrane amphiphilic molecules 6 through 11 mentioned above. A plurality of disulfide groups can be introduced. When a disulfide groups is introduced to a binding site, it is preferable to introduce the disulfide group to the binding site B.

When the disulfide group is cleaved by an in vivo or intracellular reduction action, for example, reduction by cysteine or glutathione, the hydrophilic-hydrophobic balance of the amphiphilic molecules is shifted toward hydrophilicity and thus the cleaved amphiphilic molecules are released. The present invention utilizes this phenomenon.

Techniques used to promote releasing of amphiphilic molecules from a molecular assembly by an external environmental change use, for example, shear stress, vibration, photoreaction, radical reaction, peroxidation by active oxygen, surfactation derived from a biological organism, and the like, but are not limited to these.

Hereinafter, the present invention is described as below in more detail by way of examples, whereas the present invention is not just limited to these examples.

Example 1

In this example, a compound having polyethylene glycol (PEG) in a hydrophilic part and two alkyl groups in a hydrophobic part using lysine as a spacer (corresponding to the binding site B) was synthesized.

(A) First, a protection group was introduced to a carboxyl group of lysine as follows. L-lysine (5.1 g, 35.2 mmol), p-toluenesulfonic acid (14.7 g, 77.3 mmol) and benzylalcohol (14.0 g, 124.1 mmol) were dissolved in benzene (30 mL) as a solvent, and refluxed at 100° C. for 6 hours while removing the generated water. After the solvent was removed in vacuo, the residue was purified 3 times by reprecipitation with diethylether. The purification product was recrystallized at 4° C. with a methanol/diethylether mixed solvent, filtered, and dried to obtain a lysine derivative 1 (compound 1) having the carboxyl group protected by benzylester as a white solid (18.0 g, yield: 88%).

Compound 1

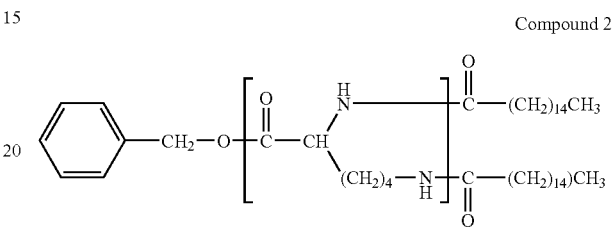

Analysis results of the lysine derivative 1:
Thin layer chromatography (silica gel plate, chloroform/methanol (4/1) (volume/volume): $R_f$: 0.2 (monospot).
Infrared absorption spectrum (cm$^{-1}$): 3034; 2952 [$v_{N-H}$ (NH$_3^+$)]; 1749 [$v_{C=O}$ (ester)]; 1600 [$\delta_{N-H}$ (NH$_3^+$)].
$^1$H-NMR spectrum (DMSO-d6, 500 MHz, δ (ppm)): 1.28, 1.40 (m, 2H, lysβ-CH$_2$); 1.51 (m, 2H, lysγ-CH$_2$); 1.80 (m, 2H, lysδ-CH$_2$); 2.29 (s, 6H, —CH$_3$); 2.70 (m, 2H, lysε-CH$_2$); 4.09 (s, 1H, lysα-CH$_2$); 5.25 (s, 2H, —CH$_2$); 7.12, 7.48 (8H, p-Tos-aroma.); 7.35-7.42 (5H, aroma.); 7.67, 8.38 (s, 6H, —NH$_3^+$).

(B) An alkyl group was introduced as a hydrophobic group to an amino group of the lysine derivative 1 as follows. Palmitic acid (3.2 g, 12.4 mmol) and N,N'-dicyclohexylcarbodiimide (2.6 g, 12.4 mmol) were dissolved in chloroform as a solvent and stirred at 25° C. for 30 minutes. Then, the lysine derivative 1 (3.0 g, 5.12 mmol) and triethylamine (1.2 g, 11.4 mmol) were added thereto. After the reaction mixture was stirred at 4° C. for 12 hours and filtered with a glass filter (G4), the solvent was removed in vacuo. The residue was re-dissolved in chloroform (100 mL) and washed 3 times with a saturated aqueous solution of sodium carbonate and 3 times with water. After the chloroform layer was dewatered with anhydrous sodium sulfate, the solvent was removed in vacuo. The resultant substance was recrystallized at 4° C. with methanol (200 mL), filtered, and then dried to obtain a lysine derivative 2 (compound 2) having the alkyl group bound to each amino group by an amide bond as a white solid (2.9 g, yield: 79%).

Compound 2

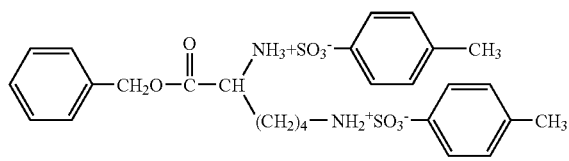

Analysis results of the lysine derivative 2:
Thin layer chromatography (silica gel plate, chloroform/methanol (4/1) (volume/volume): $R_f$: 0.53 (monospot).
Infrared absorption spectrum (cm$^{-1}$): 3311 [$v_{N-H}$ (amide)]; 1748 [$\theta_{C=O}$ (ester)]; 1640 [$v_{C=O}$ (amide)]; 1553 [$\delta_{N-H}$ (amide)].
$^1$H-NMR spectrum (CDCl$_3$, 500 MHz, δ (ppm)): 0.85 (t, 6H, —CH$_3$); 1.23 (s, 50H, —CH$_2$—CH$_2$—, lysγ-CH$_2$); 1.46 (m, 2H, lysδ-CH$_2$); 1.58 (m, 4H, —N—CO—C—CH$_2$—); 1.66, 1.82 (m, 2H, lysβ-CH$_2$); 2.12, 2.20 (t, 4H, —N—CO—CH$_2$—); 3.16 (m, 2H, lysε-CH$_2$); 4.58 (s, 1H, lysα-CH$_2$); 5.13 (s, 2H, —CH$_2$); 5.65 (br, 1H, —NH—CO—); 6.16 (d, 1H, —NH—CO—); 7.29-7.37 (5H, aroma.).

(C) The lysine derivative 2 (1.52 g, 2.13 mmol) was dissolved in a chloroform/methanol mixed solvent (10/7 (volume/volume)), and a 1N aqueous solution of sodium hydroxide (3.4 mL) was added thereto. The reaction mixture was stirred at 25° C. for 4 hours, a 1N aqueous solution of hydrochloric acid was added (up to pH 3.0), and the solvent was removed in vacuo. The residue was washed with water and methanol, and dried to obtain a dipalmitoyllysine derivative 3 (compound 3) as a white solid (1.3 g, yield: 98%).

Compound 3

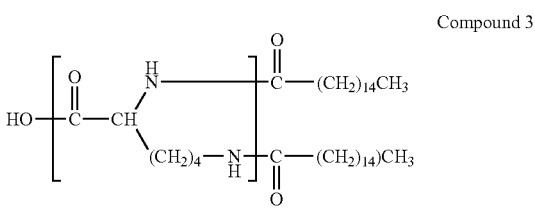

Analysis results of the dipalmitoyllysine derivative 3:
Thin layer chromatography (silica gel plate, chloroform/methanol (4/1) (volume/volume): $R_f$: 0.45 (monospot).
Infrared absorption spectrum (cm$^{-1}$): 3305 [$v_{N-H}$ (amide)]; 1721 [$v_{C=O}$ (carbonyl)]; 1638 [$v_{C=O}$ (amide)]; 1553 [$\delta_{N-H}$ (amide)].
$^1$H-NMR spectrum (CDCl$_3$, 500 MHz, δ (ppm)): 0.84 (t, 6H, —CH$_3$); 1.24 (s, 50H, —CH$_2$—CH$_2$—, lysγ-CH$_2$); 1.36 (m, 2H, lysδ-CH$_2$); 1.47 (m, 4H, —N—CO—C—CH$_2$—); 1.55, 1.67 (m, 2H, lysβ-CH$_2$); 2.02, 2.09 (t, 4H, —N—CO—

CH$_2$—); 2.99 (m, 2H, lysε-CH$_2$); 4.14 (s, 1H, lysα-CH$_2$); 7.55 (br, 1H, —NH—CO—); 7.78 (d, 1H, —NH—CO—); 12.23 (br, 1H, —COOH).

MS (LCQ): calculated value on C38H74N2O4: 623.0; measured value on C38H74N2O4: 623.5 (M$^+$H)$^+$.

(D) White solid dialkyllysine derivatives (dimyristoyllysine derivative 4 (compound 4) and distearoyl derivative 5 (compound 5)) were obtained in substantially the same operation as in (B) and (C) except that myristic acid and stearic acid were used instead of palmitic acid, respectively.

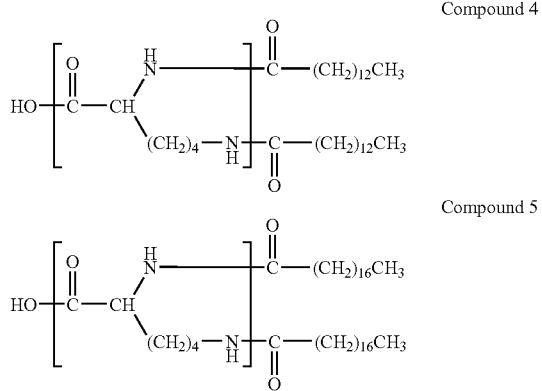

Compound 4

Compound 5

Analysis results of the dimyristoyllysine derivative 4:

Thin layer chromatography (silica gel plate, chloroform/methanol (4/1) (volume/volume): R$_f$: 0.40 (monospot).

Infrared absorption spectrum (cm$^{-1}$): 3305 [ν$_{N—H}$ (amide)]; 1721 [ν$_{C=O}$ (carbonyl)]; 1638 [ν$_{C=O}$ (amide)]; 1553 [δ$_{N—H}$ (amide)].

$^1$H-NMR spectrum (CDCl$_3$, 500 MHz, δ (ppm)): 0.84 (t, 6H, —CH$_3$); 1.24 (s, 42H, —CH$_2$—CH$_2$—, lysγ-CH$_2$); 1.36 (m, 2H, lysδ-CH$_2$); 1.47 (m, 4H, —N—CO—C—CH$_2$—); 1.55, 1.67 (m, 2H, lysβ-CH$_2$); 2.02, 2.09 (t, 4H, —N—CO—CH$_2$—); 2.99 (m, 2H, lysε-CH$_2$); 4.14 (s, 1H, lysα-CH$_2$); 7.55 (br, 1H, —NH—CO—); 7.78 (d, 1H, —NH—CO—); 12.23 (br, 1H, —COOH).

Analysis results of the distearoyl derivative 5:

Thin layer chromatography (silica gel plate, chloroform/methanol (4/1) (volume/volume): R$_f$: 0.53 (monospot).

Infrared absorption spectrum (cm$^{-1}$): 3305 [ν$_{N—H}$ (amide)]; 1721 [ν$_{C=O}$ (carbonyl)]; 1638 [ν$_{C=O}$ (amide)]; 1553 [δ$_{N—H}$ (amide)].

$^1$H-NMR spectrum (CDCl$_3$, 500 MHz, δ (ppm)): 0.84 (t, 6H, —CH$_3$); 1.24 (s, 56H, —CH$_2$—CH$_2$—, lysγ-CH$_2$); 1.36 (m, 2H, lysδ-CH$_2$); 1.47 (m, 4H, —N—CO—C—CH$_2$—); 1.55, 1.67 (m, 2H, lysβ-CH$_2$); 2.02, 2.09 (t, 4H, —N—CO—CH$_2$—); 2.99 (m, 2H, lysε-CH$_2$); 4.14 (s, 1H, lysα-CH$_2$); 7.55 (br, 1H, —NH—CO—); 7.78 (d, 1H, —NH—CO—); 12.23 (br, 1H, —COOH).

(E) The dipalmitoyllysine derivative 3 and polyethylene glycol were bound to each other as follows. The dipalmitoyllysine derivative 3 (125 mg, 0.2 mmol) and DCC (41 mg, 0.2 mmol) were dissolved in chloroform and stirred at 4° C. for 1 hour. Then, the resultant mixture was dropped to a chloroform solution of monomethoxyaminopolyethylene glycol (500 mg, 0.1 mmol) with a molecular weight of 5000 and dimethylaminopyridine (24 mg, 0.2 mmol) dissolved therein. After the reaction mixture was stirred at 25° C. for 6 hours and filtered with a glass filter (G4), the filtrate was dropped to diethylether. The precipitate was recovered by filtering, and dried. Then, an amphiphilic molecule 6 (compound 6) was isolated (500 mg, yield: 88%) with a silica gel column (solvent: chloroform/methanol=6/1 (volume/volume)).

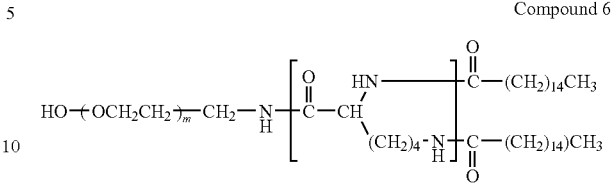

Compound 6

Analysis results of the compound 6:

Thin layer chromatography (silica gel plate, chloroform/methanol (4/1) (volume/volume): R$_f$: 0.73 (monospot).

Infrared absorption spectrum (cm$^{-1}$): 3294 [ν$_{N—H}$ (amide)]; 1634 [ν$_{C=O}$ (amide)]; 1553 [δ$_{N—H}$ (amide)].

$^1$H-NMR spectrum (CDCl$_3$, 500 MHz, δ (ppm)): 0.88 (t, 6H, —CH$_3$); 1.25 (s, 50H, —CH$_2$—CH$_2$—, lysγ-CH$_2$); 1.32 (m, 2H, lysδ-CH$_2$); 1.63-1.80 (8H, —CH$_2$—C—N—, —N—CO—C—CH$_2$—, lysβ-CH$_2$); 2.27, 2.38 (t, 4H, —N—CO—CH$_2$—); 3.29 (m, 2H, lysε-CH$_2$); 3.38 (3H, —O—CH$_3$); 3.43 (2H, —CH$_2$—NH—); 3.66 (PEG); 4.39 (s, 1H, lysα-CH$_2$).

$^{13}$C-NMR (CDCl$_3$, 500 MHz, δ (ppm)): 14.12; 22.68; 25.74; 28.75; 29.34; 29.53; 29.65; 31.92; 36.35; 38.13; 59.02; 70.44; 71.95.

(F) The following compounds were obtained by substantially the same operation as in (E) above with different combinations of the molecular weight of polyethylene glycol (PEG) and the carbon number of the hydrophobic group.

Analysis results of P50-2C14: PEG molecular weight (5000); hydrophobic group (—(CH$_2$)$_{14}$CH$_3$×2)

Thin layer chromatography (silica gel plate, chloroform/methanol (4/1) (volume/volume): R$_f$: 0.55 (monospot).

Infrared absorption spectrum (cm$^{-1}$): 3294 [ν$_{N—H}$ (amide)]; 1634 [ν$_{C=O}$ (amide)]; 1553 [δ$_{N—H}$ (amide)].

$^1$H-NMR spectrum (CDCl$_3$, 500 MHz, δ (ppm)): 0.88 (t, 6H, —CH$_3$); 1.25 (s, 46H, —CH$_2$—CH$_2$—, lysγ-CH$_2$); 1.32 (m, 2H, lysδ-CH$_2$); 1.63-1.80 (8H, —CH$_2$—C—N—, —N—CO—C—CH$_2$—, lysβ-CH$_2$); 2.15, 2.23 (t, 4H, —N—CO—CH$_2$—); 3.29 (m, 2H, lysε-CH$_2$); 3.38 (3H, —O—CH$_3$); 3.43 (2H, —CH$_2$—NH—); 3.66 (PEG); 4.39 (s, 1H, lysα-CH$_2$).

Analysis results of P125-2C14: PEG molecular weight: (12500); hydrophobic group (—(CH$_2$)$_{14}$CH$_3$×2)

Thin layer chromatography (silica gel plate, chloroform/methanol (4/1) (volume/volume): R$_f$: 0.50 (monospot).

Infrared absorption spectrum (cm$^{-1}$): 3294 [ν$_{N—H}$ (amide)]; 1634 [ν$_{C=O}$ (amide)]; 1553 [δ$_{N—H}$ (amide)].

$^1$H-NMR spectrum (CDCl$_3$, 500 MHz, δ (ppm)): 0.88 (t, 6H, —CH$_3$); 1.25 (s, 46H, —CH$_2$—CH$_2$—, lysγ-CH$_2$); 1.32 (m, 2H, lysδ-CH$_2$); 1.63-1.80 (8H, —CH$_2$—C—N—, —N—CO—C—CH$_2$—, lysβ-CH$_2$); 2.15, 2.23 (t, 4H, —N—CO—CH$_2$—); 3.29 (m, 2H, lysε-CH$_2$); 3.38 (3H, —O—CH$_3$); 3.43 (2H, —CH$_2$—NH—); 3.66 (PEG); 4.39 (s, 1H, lysα-CH$_2$).

Analysis results of P125-2C16: PEG molecular weight (12500); hydrophobic group (—(CH$_2$)$_{16}$CH$_3$×2)

Thin layer chromatography (silica gel plate, chloroform/methanol (4/1) (volume/volume): R$_f$: 0.63 (monospot).

Infrared absorption spectrum (cm$^{-1}$): 3305 [ν$_{N—H}$ (amide)]; 1638 [ν$_{C=O}$ (amide)]; 1556 [δ$_{N—H}$ (amide)].

$^1$H-NMR spectrum (CDCl$_3$, 500 MHz, δ (ppm)): 0.88 (t, 6H, —CH$_3$); 1.25 (s, 50H, —CH$_2$—CH$_2$—, lysγ-CH$_2$); 1.32 (m, 2H, lysδ-CH$_2$); 1.63-1.80 (8H, —CH$_2$—C—N—, —N—CO—C—CH$_2$—, lysβ-CH$_2$); 2.27, 2.38 (t, 4H, —N—CO—CH$_2$—); 3.29 (m, 2H, lysε-CH$_2$); 3.38 (3H, —O—CH$_3$); 3.43 (2H, —CH$_2$—NH—); 3.66 (PEG); 4.39 (s, 1H, lysα-CH$_2$).

Example 2

In this embodiment, the introduction stability of the lysine-type PEG-bound lipid (hereinafter, referred to as "PEG-bound lipid") obtained in Example 1 to a vesicle, and the effect by the PEG-bound lipid of suppressing the aggregate of the vesicle, were clarified based on the correlation with the PEG-bound lipid structure.

An aqueous solution of PEG-bound lipid (17.0 μM, 22.6 mL) was mixed with a vesicle dispersion (17.0 mM, 15.0 mL) and stirred at 37° C. to obtain a dispersion of PEG-bound lipid-introduced vesicle. The dispersion of PEG-bound lipid-introduced vesicle was diluted 6 folds with phosphoric acid buffer saline (PBS, pH 7.0), and the introduction amount was measured time-dependently until 12 hours later. The introduction amount can be calculated as follows (Yoshioka, H., Biomaterials 1991, 12, 861).

The dispersion of PEG-bound lipid-introduced vesicle was subjected to ultracentrifugation (33,000 rpm, 30 min.) to separate unintroduced PEG-bound lipid, then dried in vacuo, and dissolved in CDCl$_3$. An undissolved component was removed with a PTFE filter (0.2 μm), and then $^1$H-NMR measurement was performed. Using the area ratio of DPPC choline methyl proton (δ=3.36 ppm) and PEG chain methylene proton (δ=3.64 ppm), the introduction ratio was calculated. Where the integral value of the PEG chain methylene proton treated with ultracentrifugation is H$_{PEG+}$ and the integral value of the PEG chain methylene proton not treated with ultracentrifugation is H$_{PEG-}$ with the integral value of the vesicle choline methyl proton being fixed, and the concentration of the PEG lipid is A (mol %), the introduction amount of the PEG lipid can be calculated based on the following formula.

[PEG–lipid]=$A$×($H_{PEG+}/H_{PEG-}$)(mol %)

Release Behavior of the PEG Lipid from the Vesicle

Figure 2:
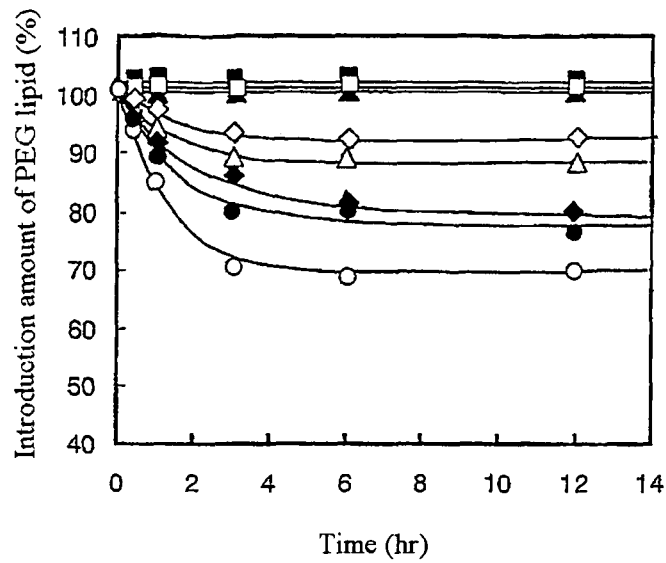
FIG. 2 is a graph for comparing the release behavior of PEG lipids from vesicle.

FIG. 2 shows the observation results ($^1$H-NMR) of the release behavior of the PEG-bound lipid from the vesicle after 6-fold dilution with PBS (pH 7.0). The symbols in FIG. 2 represent the following: (●): P50-2C14; (○): P125-2C14; (▲): P50-2C16; (△): P125-2C16; (□): P125-2C18; (■): P125-4C16; (◆): P50-DPPE; and (◇): P125-DSPE. Regarding the double chain PEG lipid, P125-2C18 (PEG molecular weight (12500); hydrophobic group (—(CH$_2$)$_{16}$CH$_3$×2)), P125-4C16 (PEG molecular weight (12500); hydrophobic group (—(CH$_2$)$_{14}$CH$_3$×4)), and P50-2C16 (PEG molecular weight (5000); hydrophobic group (—(CH$_2$)$_{14}$CH$_3$×2)) were not recognized to be released. P125-DSPE (PEG-bound lipid having PEG molecular weight (12500) bound to distearoylphosphatidylethanolamine (DSPE)) and P125-2C16 (PEG molecular weight (12500); hydrophobic group (—(CH$_2$)$_{14}$CH$_3$×2)) were separated from the vesicle 3 hours later by about 8% and about 10%, respectively. P50-2C14 (PEG molecular weight (5000); hydrophobic group (—(CH$_2$)$_{12}$CH$_3$×2)) and P125-2C14 (PEG molecular weight (12500); hydrophobic group (—(CH$_2$)$_{12}$CH$_3$×2)) were released from the vesicle 12 hours later by about 20% and about 30%, respectively. By increasing the molecular weight of the PEG chain or shortening the alkyl chain, the PEG chain on the surface of the liposome was made more likely to be released which increased the controllability and directivity on the residing characteristics in blood.

P50-2C16 was not recognized to be release, whereas P50-DPPE (PEG molecular weight (5000); hydrophobic group (—(CH$_2$)$_{16}$CH$_3$×2)) was released by about 20%. P50-DPPE is a PEG-bound lipid having PEG molecular weight (5000) bound to dipalmitoylphosphatidylethanolamine. It is considered that PEG-DPPE is influenced by an increase of hydrophilicity of the entire lipid due to the hydrophilicity of the head part of the phospholipid. By contrast, it is considered that the lysine-type PEG lipid is not influenced by such an increase, and the hydrogen bond of the amide bond part and the vesicle phospholipid ester part in the lysine backbone contributes to the stable introduction.

Example 3

1. Synthesis of Novel Transmembrane-Type Lipid

Diamino PEG (M.w.=220) was used as the starting material, and one terminus was first protected with a t-butoxy (Boc) group. With a benzyloxycarbonyl (Z) group, the disulfide in the hydrophobic part may be severed in the final deprotection procedure (catalytic reduction or strong acid). This is why the Boc group was selected with which deprotection is possible even with a weak acid. In order to prevent the cleavage of the Boc group, contamination of acid and heating were avoided as much as possible.

4,7,10-Trioxa-1,13-tridecanediamine (6.6 g, 30 mmol) and triethylamine (TEA, 1.5 g, 15 mmol) were dissolved in 20 mL distilled chloroform, and a distilled chloroform solution (100 mL) of anhydrous t-butoxycarbonyl ((Boc)$_2$O, 3.3 g, 15 mmol) was gradually dropped thereto to cause a reaction. After the resultant mixture was stirred at 4° C. for 6 hours, the solvent was removed in vacuo, and the residue was re-dissolved in benzene to filter out an insoluble salt component. The resultant substance was purified with a silica gel column (neutral, solvent: chloroform/methanol (4/1) (volume/volume)) to obtain a PEG lipid derivative (7) (compound 7) having only one terminus protected with the Boc group as a pale yellow viscous liquid (2.4 g, yield: 50%).

Compound 7

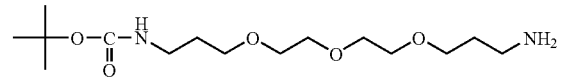

Analysis results of the PEG lipid derivative 7:

Thin layer chromatography (silica gel plate, chloroform/methanol (4/1) (volume/volume): R$_f$: 0.27 (monospot).

Infrared absorption spectrum (cm$^{-1}$): 3363 ($v_{N-H}$); 1709 ($v_{C=O}$); 1520 ($v_{N-H}$); 1271 ($v_{C-O}$).

$^1$H-NMR (CDCl$_3$, 500 MHz, δ (ppm)): 1.43 (s, 9H, t-butyl); 1.71-1.78 (m, 4H, —CH$_2$—C—N—); 2.75-2.81 (t, 2H, —CH$_2$—N); 3.20-3.39 (br, 2H, —CH$_2$—N—); 3.49-3.65 (m, 12H, POE).

2,2'-Dipyridyl disulfide (2-PD, 4.3 g, 19.2 mmol) was stirred in 20 mL distilled THF for 1 hour in a nitrogen atmosphere to be deoxygenated, and then a THF solution (10 mL) of 1,10-decanedithiol (1.0 g, 4.8 mmol) was gradually dropped thereto to allow a thiol-disulfide exchange reaction at 37° C. for 10 hours. As a result, a PD group was introduced to both termini of 1,10-decanedithiol (0.82 g, yield: 40%). The solvent was removed in vacuo, and purification was performed with a flash column (silica gel, solvent: chloroform/ethyl acetate (10/1) (volume/volume)). 4 equivalents of 2-PD was taken with respect to 1,10-decanedithiol, but it is considered that the yield was decreased because a by-product having an alkyl chain several times longer was obtained. The structure of a compound 8 was confirmed by ¹NMR, ESI-MS. The compound 8 (0.77 g, 1.8 mmol) was again stirred in 20 mL distilled THF for 1 hour in a nitrogen atmosphere to be deoxygenated, and then a THF solution (20 mL) of 10-carboxy-1-decanethiol (0.79 g, 3.6 mmol) was gradually dropped thereto to allow a reaction for 10 hours. Reprecipitation was performed with diethylether twice for purification. The purified product was recrystallized with chloroform to obtain a dicarboxylic acid derivative 9 (compound 9) having a carbon chain length of 30 as a white solid (1.1 g, yield: 93%).

amide bond. The solution was separated with a 4% aqueous solution of citric acid and water (chloroform phase was sampled), and the solvent was removed in vacuo. Then, the purification was performed with a flash column (silica gel, solvent: chloroform/acetone (2/1) (volume/volume)) to obtain a compound 10 as a white solid (0.35 g, yield: 91%).

Compound 10

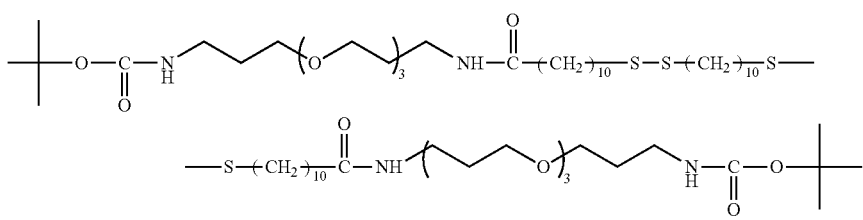

Analysis results of the compound 10:

Thin layer chromatography (silica gel plate, chloroform/acetone (2/1) (volume/volume): $R_f$: 0.44 (monospot).

¹H-NMR (CDCl₃, 500 MHz, δ (ppm)): 1.28-1.37 (m, 36H, —CH₂—); 1.44 (s, 18H, t-butyl); 1.56-1.70 (m, 12H, —CH₂—C—CO—/—CH₂—C—S—); 1.73-1.80 (m, 8H, —CH₂—C—N—); 2.13-2.16 (t, 4H, —CH₂—CO—); 2.66-2.69 (t, 8H, —CH₂—S—); 3.31-3.22 (m, 4H, —CH₂—NH—COO—); 3.33-3.37 (q, 4H, —CH₂—NH—); 3.53-3.66 (m, 24H, POE).

The compound 10 (0.156 g, 0.125 mmol) was dissolved in 5 mL dichloromethane, and 2.6-lutidine (0.82 mL, 1.5 M) and trimethylsilyl triflate (0.89 mL, 1 M) were added thereto. The resultant substance was stirred at room temperature for 1 hour. After appearance of an amino group was detected with ninhydrin spray, the solvent was removed at 60 to 70° C. in vacuo with an acid-resistant pump. The resultant substance was washed twice with water, and reprecipitation was performed with diethylether for purification to obtain a transmembrane-type lipid (11) (compound 11) as a pale yellow solid (0.12 g, yield: 93%).

Compound 8

Compound 9

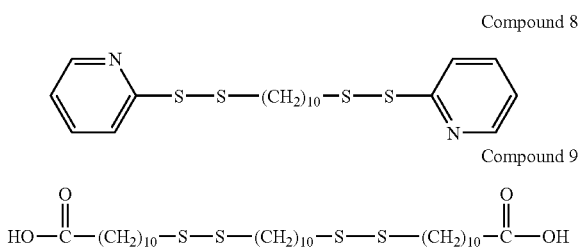

Analysis results of the compounds 8 and 9:

(Compounds 8): Thin layer chromatography (silica gel plate, chloroform/ethyl acetate (10/1) (volume/volume): $R_f$: 0.7 (monospot).

¹H-NMR (CDCl₃, 500 MHz, δ (ppm)): 1.23-1.38 (m, 12H, —CH₂—); 1.65-1.71 (m, 4H, —S—C—CH₂—); 2.79 (t, 4H, —S—CH₂—); 7.05-8.46 (m, 8H, —C₅H₄).

(Compounds 9): Thin layer chromatography (silica gel plate, chloroform/acetone (4/1) (volume/volume): $R_f$: 0.23 (monospot).

Infrared absorption spectrum (cm⁻¹): 3038 ($v_{O-H}$); 1694 ($v_{C=O}$); 1229 ($v_{C-O}$).

¹H-NMR (CDCl₃, 500 MHz, δ (ppm)): 1.29-1.39 (m, 36H, —CH₂—); 1.61-1.70 (m, 12H, —CH₂—C—CO—, —CH₂—C—S—); 2.35 (t, 4H, —CH₂—CO—); 2.68 (t, 8H, —CH₂—S—).

The dicarboxylic acid derivative (compound 9) (0.20 g, 0.31 mmol), BOP reagent (0.30 g, 0.69 mmol), TEA (0.22 g, 2.2 mmol) and PEG having an amino group at one terminus (compound 7) (0.74 g, 2.3 mmol) were reacted with one another in 20 mL distilled chloroform for 12 hours to form an Compound 11

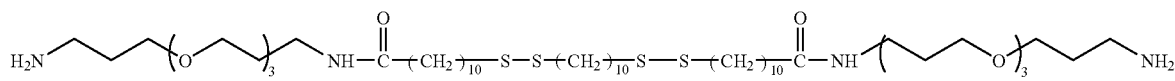

Analysis results of the transmembrane-type lipid (11):

Thin layer chromatography (silica gel plate, chloroform/methanol (4/1) (volume/volume): $R_f$: 0.19 (monospot).

Infrared absorption spectrum (cm⁻¹): 3326 ($v_{N-H}$); 1637 ($v_{C=O}$); 1540 ($v_{N-H}$); 1252 ($v_{C-O}$); 1114 ($v_{C-O-C}$); 1314 ($v_{C-S}$).

¹H-NMR (CDCl₃, 500 MHz, δ (ppm)): 1.28-1.43 (m, 36H, —CH₂—); 1.59-1.80 (m, 20H, —CH₂—C—CO—/—CH₂—C—S—/—CH₂—C—N); 2.13-2.16 (t, 4H, —CH₂—CO—); 2.66-2.69 (t, 8H, —CH₂—S—); 2.87-2.89 (t, 4H, —CH₂—NH—C—O—); 3.32-3.36 (q, 4H, —CH₂—NH—); 3.54-3.65 (m, 24H, POE).

2. Preparation of Protein-Bound Liposome

To a lipid mixture of DPPC (1.0 g, 1.36 mmol), cholesterol (0.42 g, 1.09 mmol) and DPEA (0.19 g, 0.27 mmol), the transmembrane-type lipid (11) (8.5 mg, 8.16 μmol) was mixed at 0.3 mol %, and the resultant substance was dissolved in 5 mL benzene and then lyophilized. After benzene was removed, the resultant substance was hydrated in phosphoric acid buffer saline (PBS) such that the lipid concentration would be about 2 wt. % (r.t., over night). Then, the resultant solution was freeze-thawed and extruded through pores down to a pore having a final diameter of 50 nm by an extrusion method. After the external aqueous phase was washed away by ultracentrifugation, the concentration was adjusted based on the phospholipid quantification value to prepare a monolayer liposome having a particle diameter of about 140 nm.

3. Measurement of the Introduction Amount of the Transmembrane-Type Lipid

The introduced amount was quantified by a fluorescence measurement. The amino group at both termini of the transmembrane-type lipid was labeled with fluorescamine. In order to prove that the lipid is extended throughout the membrane, (a) only the amino group on the surface of the liposome and (b) all the amino group in the liposome were measured and compared.

THF and fluorescamine (42 mg, 0.15 mmol) were added to Glu2C16 (30 mg, 50 μmol), stirred for 15 minutes and diluted. Then, a calibration curve ($R^2$=0.9994) was created by fluorescence measurement ($\lambda_{ex}$=390 nm, $\lambda_{em}$=475 nm).

(a) 100 μL of fluorescamine (10 mg/500 μL acetone) was added to a liposome dispersion ([DPPC]=1 wt. %, 1 mL) and stirred for 15 minutes, and then unreacted fluorescamine was removed by ultracentrifugation. The resultant substance was re-dissolved in THF, and fluorescence measurement ($\lambda_{ex}$=390 nm, $\lambda_{em}$=475 nm) was performed.

(b) A liposome dispersion ([DPPC]=1 wt. %, 1 mL) was dissolved in THF, and 100 μL of fluorescamine (10 mg/500 μL acetone) was added thereto and stirred for 15 minutes. Then, fluorescence measurement ($\lambda_{ex}$=390 nm, $\lambda_{em}$=475 nm) was performed.

[Results]
According to the fluorescence measurement, the amino group on the surface of the liposome was about 50% of the entire amino group (Table 1). As a result of this, and in consideration that a long chain alkyl is likely to assume a extended conformation in order to minimize the methylene-to-methylene steric hindrance, it can be concluded that the synthetic lipid now introduced is extended throughout the bilayer of the liposome and are immobilized in the membrane and the amino group at the terminal are sufficiently exposed on the surface of the liposome.

TABLE 1

Amount of amino group in the liposome

| | |
|---|---|
| Outer amino group of liposome (mol %) | 0.20 |
| Total amino group of liposome (mol %) | 0.42 |
| Exposed amino group (%) | 48 |
| Outer amino group per liposome (×$10^2$) | 6.5 |

4. Introduction of Protein to the Surface of the Liposome

To the amino group on the surface of the prepared liposome, model protein labeled with fluoresceinisothiocyanate (FITC) (α-lactalbumin (molecular weight: 14 kDa), rHSA (66.5 kDa), IgG (150 kKa), ferritin (460 kDa), thyroglobulin (670 kDa)) was bound using a crosslinker N-succinimidyl 3-(2-pyridyltdithio) propionate (SPDP) and N-succinimidyl 3-maleimidopropionate (SMDP). For the protein, protein having a closer isoelectric point was selected from electrophoresis markers in order to analyze the molecular weight dependence (Table 2).

TABLE 2

| | Protein characteristics | |
|---|---|---|
| | M.w.(kDa) | Isoelectric point |
| α-Lactalbumin | 14 | 4.1-4.8 |
| rHSA | 66.5 | 5.1 |
| IgG | 150 | |
| Ferritin | 460 | 4.0-5.0 |
| Thyrogrobulin | 670 | 4.5 |

[Preparation of Protein]
8 μL (1.5 eq) of SPDP (3.8 mg/Ethanol 2 ml) was added to protein 2.0 g/dL (1 mL, PBS) and stirred at room temperature for 30 minutes. Then, 200 μL (5 eq) of FITC (6 mg/1N NaOH 250 μL, PBS 750 μL) was added thereto and stirred at room temperature for another 30 minutes. Unreacted SPDP and FITC were removed by gel column chromatography (Sephadex G25). 40 μL (20 mM) of DTT (15.4 mg/PBS 1 mL) was added and stirred for 30 minutes, and then unreacted DTT was removed by gel column chromatography (Sephadex G25).

[Preparation of SMDP-Bound Liposome]
38 μL of SMDP (30 mg/500 μL DMF) was added to a dispersion of transmembrane-type lipid-introduced liposome (PBS 5 mL, [DPPC]=2.8 g/dL) and stirred at room temperature for 1 hour. Unreacted SMDP was removed by ultracentrifugation (33,000 rpm, 60 min.×2).

[Preparation of Protein-Bound Liposome]
1 mL of an SPDP-introduced protein solution (0.4 g/dL) was added to a dispersion of SMDP-introduced liposome (PBS 4 mL, [Lipid]=0.6 g/dL) and stirred at 4° C. for 12 hours. Unreacted protein was removed by ultracentrifugation (10,000 rpm, 5 min.×3). Then, 5 types of protein were each bound to the surface of the liposome.

[Quantification of the Bound Protein]
A dispersion of the prepared protein-bound liposome was dissolved in an ethanol solution, and the fluorescence intensity of the solution ($\lambda_{ex}$=490 nm, $\lambda_{em}$=520 nm) was measured. Thus, the number of protein conjugated to the surface of the liposome, and the conjugation ratio of the protein to the amino group on the surface of the liposome were calculated (Table 3).

TABLE 3

| | | Conjugation ratio of protein | |
|---|---|---|---|
| protein | Mw (kDa) | The Number of protein conjugated to a liposome | Conjugation ratio of proteins (%) |
| α-Lactalbumin | 14 | 335 | 52 |
| rHSA | 66.5 | 141 | 21 |
| IgG | 150 | 106 | 16 |
| Feritin | 460 | 59 | 10 |
| Thyrogrobulin | 670 | 46 | 7 |

5. Measurement of the Release Rate of the Protein-Bound Transmembrane-Type Lipid The prepared liposome having each of 5 types of protein (FITC-labeled) bound thereto was shaken at pH 7.4 at 37° C., and the fluorescence measurement of release behavior of the proteins was performed.

Figure 3:
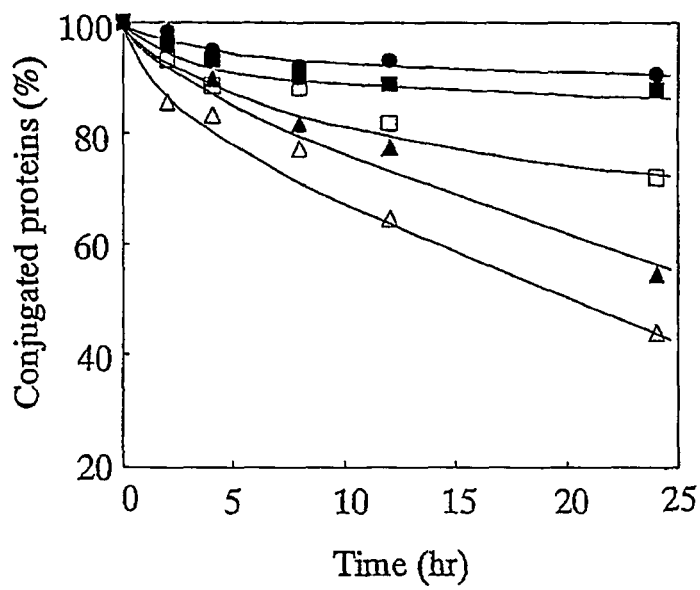
FIG. 3 is a graph for comparing the release behavior of protein-bound transmembrane-type lipids from protein-bound liposomes.

[Method of Experiment]
A dispersion of protein-bound (or protein-conjugated) liposome (PBS 10 mL, [Lipid]=0.8 g/dL, stored at 4° C.) was shaken at 37° C. 5 minutes after the start, 1 mL of control (0 min) was sampled and subjected to centrifugation (10,000 rpm, 5 min.). Then, fluorescence measurement (FITC, $\lambda_{ex}$=490 nm, $\lambda_{em}$=520 nm) of the supernatant (700 μL) was performed, and the separated protein was quantified based on the calibration curve. 2, 4, 8, 12 and 24 hours later also, the same operation was performed to measure the time-dependent change of the released protein. FIG. 3 shows the results. The symbols in FIG. 3 represent the following: (●): α-lactalbumin; (■): rHSA; (□): IgG; (▲): ferritin; and: (Δ): thyrogrobulin.

As the molecular weight of the protein was increased, the release from the surface of the liposome was accelerated. Up to rHSA having a molecular weight of 66.5 kDa, about 90% was stably retained.

6. Release Effect by Addition of a Membrane-Permeable Reductant

The α-lactalbumin-bound liposome which was least released in the above-described evaluation on release, was evaluated in terms of release in the state where L-cysteine (Cys) which is a membrane-transmissive reductant was coexistent in the external aqueous phase.

[Method of Experiment]

Figure 4:
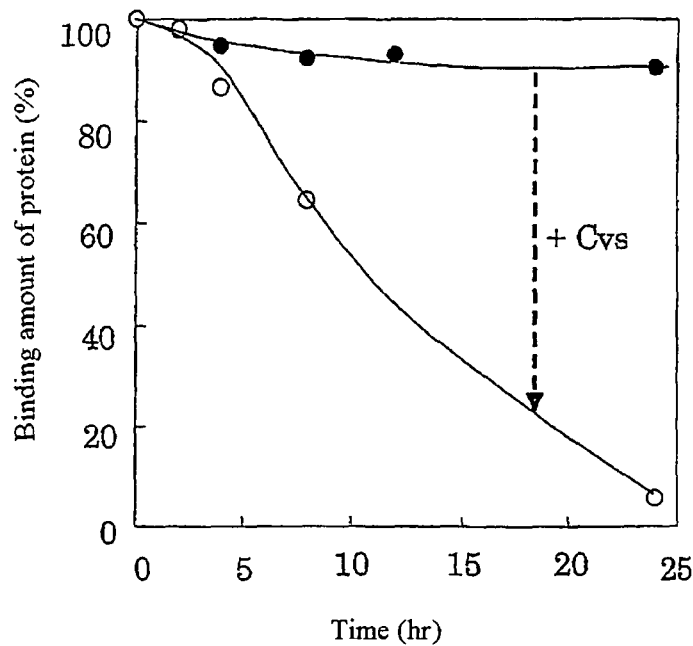
FIG. 4 is a graph for comparing the separation behavior of proteins from protein-bound liposomes when a reductant is added.

A dispersion of α-lactalbumin-bound liposome (PBS 1 mL×8 samples, [Lipid]=0.8 g/dL, stored at 4° C.) was stirred in a nitrogen atmosphere (30 min., 4° C.), and then a 20 mM Cys solution was added thereto and shaken at pH 7.4 at 37° C. 5 minutes after the start, 1 mL of control (0 min) was sampled and subjected to centrifugation (10,000 rpm, 5 min.). Then, fluorescence measurement (FITC, $\lambda_{ex}$=490 nm, $\lambda_{em}$=520 nm) of the supernatant (700 μL) was performed, and the released protein was quantified based on the calibration curve. 2, 4, 8, 12 and 24 hours later also, the same operation was performed to measure the time-dependent change of the released protein. FIG. 4 shows the results. The symbols in FIG. 4 represent the following: (●): α-lactalbumin (without Cys); and (○): α-lactalbumin+Cys solution (with Cys).

Without Cys, 90% or more was retained on the surface of the liposome even 24 hours later. By contrast, with Cys, the release of the protein was gradually accelerated, and 95% was released 24 hours later. This is considered to be a release effect caused because Cys was extended throughout the bilayer and reduced the disulfide bond of the transmembrane-type lipid introduced to the bilayer.

Example 4

1. Synthesis of Multi-Alkyl Chain-Type Glycolipid

A benzene solution (100 mL) of p-toluenesulfonic acid monohydrate (4.56 g, 24 mmol) was refluxed at 85° C., and water was removed before the reaction with the Dean-stark apparatus. Glutamic acid (2.96 g, 20 mmol) and hexadecylalcohol (10.7 g, 44 mmol) or octadecylalcohol (10.7 g, 44 mmol) were added to the reaction solution, and subjected to boiling point reflux for 10 hours while removing the generated water. As the reaction proceeded, the suspension was gradually dissolved to become transparent yellow. After the reaction completed, the solvent was removed. The resultant solution was separated 3 times with a saturated aqueous solution of sodium carbonate/chloroform, dewatered with magnesium sulfate, and recrystallized with methanol at 4° C. to obtain diacylglutamic acid derivatives 12 (compound 12) (83%) and 13 (compound 13) (85%).

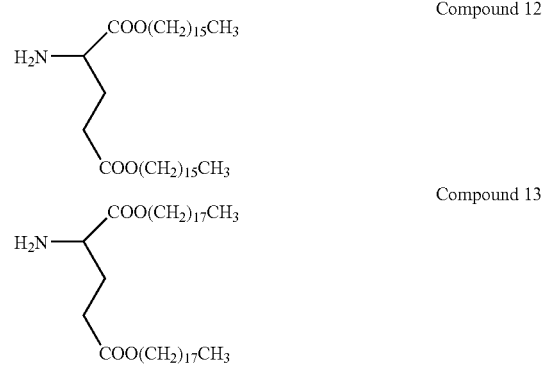

Analysis results of the diacylglutamic acid derivative 12:
Thin layer chromatography (silica gel plate, chloroform/methanol (4/1) (volume/volume): $R_f$: 0.83 (monospot).
Infrared absorption spectrum (cm$^{-1}$): 1737 ($v_{C=O}$, ester).
$^1$H-NMR (CDCl$_3$, 500 MHz, δ ppm): 0.89 (t, 6H, —CH$_3$); 1.25 (s, 52H, —CH$_2$—CH$_2$—); 1.62 (m, 4H, —CO—O—C—CH$_2$); 1.84 (m, 1H, glu β-CH$_2$); 2.08 (m, 1H, glu β-CH$_2$); 2.45 (t, 2H, glu γ-CH$_2$); 3.45 (t, 1H, glu α-CH); 4.06, 4.10 (t, 4H, —CO—O—CH$_2$)
MS (ESI) Calcd: 595.9. Found: 597.3 (MH)$^+$.

Triethylamine (5.71 mL, 41 mmol) was added to a chloroform solution (10 mL) of PEG having an amine at both termini (9.01 g, 41 mmol) and stirred at room temperature. A chloroform solution of Z chloride (6.98 g, 41 mmol) was dropped slowly (about one drop in 2 seconds) with a dropping funnel. The reaction swiftly proceeded along with the dropping, and a target product protected at one terminus ($R_f$=0.42) appeared on TLC (chloroform/methanol=4/1, silica gel plate). A by-product protected at both termini ($R_f$=0.81) was also produced. After the reaction completed, the solvent was removed, and the by-product protected at both termini and TEA hydrochloride salt were removed by column chromatography (silica gel, chloroform/methanol=4/1). The target compound (compound 14) was purified. The identification of the compound was performed by IR and $^1$H-NMR, ESI-MS. TEA salt, which is insoluble in benzene and ethyl acetate, is also possible to be removed by using the solvents.

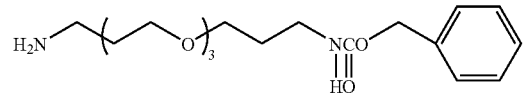

Analysis results of the compound 14:
Thin layer chromatography (silica gel plate, chloroform/methanol (4/1) (volume/volume): $R_f$: 0.42 (monospot).
Infrared absorption spectrum (cm$^{-1}$): 1713 ($v_{C=O}$, ester); 1623 ($v_{C=O}$, amide); 1528 ($δ_{N=H}$, amide).
$^1$H-NMR (CDCl$_3$, 500 MHz, δ ppm): 1.25 (br, 2H, NH$_2$—C—); 1.80 (m, 2H, NH$_2$—C—CH$_2$—); 1.94 (m, 2H, CONH—C—CH$_2$—); 3.11 (m, 2H, NH$_2$—CH$_2$—); 3.30 (q, 2H, CONH—CH$_2$—); 3.58 (t, 12H, —O—CH$_2$—); 5.08 (s, 2H, C$_6$H$_5$—CH$_2$—); 7.34 (t, 5H, C$_6$H$_5$—CH$_2$—); 7.57 (br, 1H, —CONH—)
MS (ESI) Calcd: 354.4. Found: 355.4 (MH)$^+$.

Triethylamine (196 μL, 1.4 mmol) and maltose (507 mg, 1.4 mmol) were added to a DMF solution (5 mL) of the compound 14 (500 mg, 1.4 mmol) and stirred at 70° C. for 12 hours. As the reaction proceeded, a spot of a target product ($R_f$=0.09) appeared on TLC (chloroform/methanol/water=62/25/4, silica gel plate). After the reaction completed, the solvent was removed, and the target product (compound 15) was purified by column chromatography (silica gel, chloroform/methanol/water=62/25/4). The identification of the compound was performed by IR and $^1$H-NMR, ESI-MS.

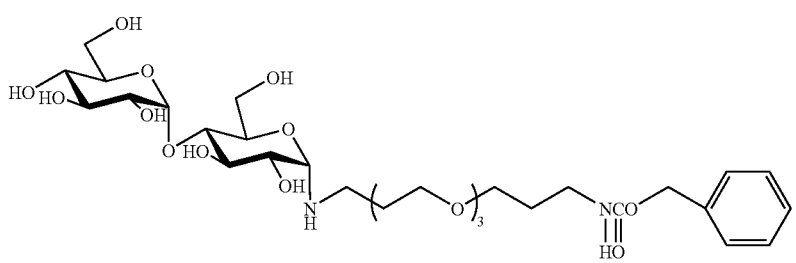

Compound 15

Analysis results of the compound 15:

Thin layer chromatography (silica gel plate, chloroform/methanol/water (65/25/4) (volume/volume): $R_f$: 0.18 (monospot).

Infrared absorption spectrum (cm$^{-1}$): 1720 ($\nu_{C=O}$, ester); 1654 ($\nu_{C=O}$, amide); 1540 ($\delta_{N-H}$, amide).

$^1$H-NMR (D2O, 500 MHz, δ ppm): 1.71 (m, 2H, NH—C—CH$_2$—); 1.84 (m, 2H, CONH—C—CH$_2$—); 3.07 (m, 2H, NH—CH$_2$—); 3.15 (m, 2H, CONH—CH$_2$—); 3.21 (t, 1H, maltoseC-4); 3.31 (t, 1H, maltoseC-4); 3.57 (t, 12H, reaction completed, DMF was removed, and a double chain glycolipid 17 ($R_f$=0.38, chloroform/methanol=10/1, silica gel plate) and a quadruple chain glycolipid 19 ($R_f$=0.50) were purified by column chromatography (silica gel, chloroform/methanol=10/1). The identification of the compounds was performed by IR and $^1$H-NMR, ESI-MS. Glycolipids having a carbon number of 18, i.e., a double chain glycolipid 18 ($R_f$=0.40, chloroform/methanol=10/1, silica gel plate) and a quadruple chain glycolipid 20 ($R_f$=0.51) were synthesized in substantially the same manner.

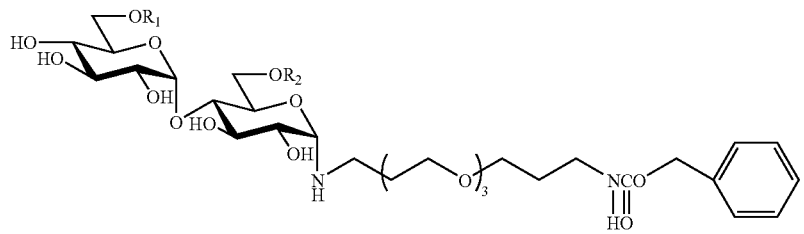

Compound 17 : n = 15
Compound 18 : n = 17
R1 or R2 = OH

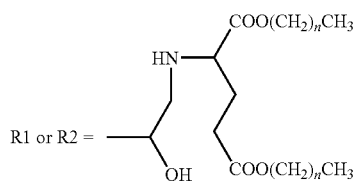

Compound 19 : n = 15
Compound 20: n = 17

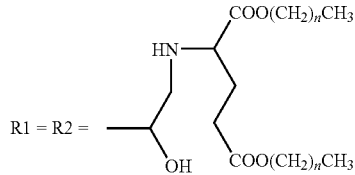

—O—CH$_2$—); 3.49-3.96 (m, 10H, maltoseC-2,3,5,6); 4.59 (d, 1H, maltoseC-1); 5.05 (br, 1H, maltoseNH—C—C—); 5.16 (d, 1H, maltoseC-1, anomericH); 5.33 (d, 2H, C$_6$H$_5$—CH$_2$—); 7.37 (t, 5H, C$_6$H$_5$—CH$_2$—); 8.39 (br, 1H, —CONH—).

MS (ESI) Calcd: 678.7. Found: 679.4 (MH)$^+$.

Triethylamine (698, 5.0 mmol) and epichlorohydrin (228 μL, 2.8 mmol) were added to a DMF solution (10 mL) of the compound 15 (1.00 g, 1.4 mmol) and stirred at 40° C. for 2 hours. As the reaction proceeded, a new spot ($R_f$=0.19, 0.27) appeared by introduction of an epoxy group on TLC (chloroform/methanol/water=65/25/4, silica gel plate). Such a compound (compound 16) was not isolated. 12(Glu2C16, 2.33 g, 3.9 mmol) was added to the resultant substance and stirred at 60° C. for 18 hours for binding to the epoxy group. After the This reaction is to introduce an alkyl chain to position-6 primary hydroxyl group using the difference in reactivity among hydroxyl groups. It was attempted to introduce 4 alkyl chains using an ester bond, but the yield was low due to the alkylglutamate-to-alkylglutamate steric hindrance and the isolation was difficult. By using an epoxy group having a higher level of activity, it was made possible to introduce four alkyl chains and perform the isolation. Thus, the synthesis of glycolipids 17 through 20 (compounds 17 through 20) was made possible.

Analysis results of the glycolipid 19 (4C16):

Thin layer chromatography (silica gel plate, chloroform/methanol (10/1) (volume/volume): $R_f$: 0.50 (monospot).

Infrared absorption spectrum (cm$^{-1}$): 1731 ($\nu_{C=O}$, ester); 1672 ($\nu_{C=O}$, amide); 1521 ($\delta_{N-H}$, amide).

$^1$H-NMR (CD$_3$OD, 500 MHz, δ ppm): 0.89 (t, 12H, —CH$_3$); 1.28 (s, 104H, —CH$_2$—CH$_2$—); 1.64 (m, 8H, —CO—O—C—CH$_2$); 1.74 (m, 4H, glu β-CH$_2$, NH—C—CH$_2$—); 2.01 (m, 2H, CONH—C—CH$_2$—); 2.14 (m, 2H, glu β-CH$_2$); 2.29-2.35 (m, 8H, NH—CH$_2$—C(OH)—C—O—, NH—C—C(OH)—CH$_2$—O—); 2.45 (m, 4H, glu γ-CH$_2$); 2.55 (m, 2H, NH—C—CH(OH)—C—O—); 3.11 (m, 2H, NH—CH$_2$—); 3.18 (m, 2H, CONH—CH$_2$—); 3.49-3.74 (m, 12H, maltoseC-2,3,4,5,6); 3.51 (m, 14H, —O—CH$_2$—, glu α-CH); 4.06 (t, 2H, maltoseC-1); 4.15 (t, 4H, —CO—O—CH$_2$); 4.27 (t, 4H, —CO—O—CH$_2$); 5.05 (m, 2H, C$_6$H$_5$—CH$_2$—); 7.33 (t, 5H, C$_6$H$_5$—CH$_2$—); 8.01 (br, 1H, —CONH—).

MS (ESI) Calcd: 1981.4. Found: 1981.4 (MH)$^+$.

Pd black powder (20 mg) (or Pd/C powder) was added to an ethanol solution (3 mL) of the compound 17 (20 mg, 10 nmol) and stirred at room temperature for 4 hours with a passage of H$_2$ gas (generated with Zn/H$_2$SO$_4$). As the reaction proceeded, a positive ninhydrin spot 21 (R$_f$=0.09, chloroform/methanol=10/1, silica gel plate) appeared on TLC. After the reaction completed, the Pd powder was filtered and the solvent was removed. Then, the target compound 21 was purified by column chromatography (silica gel, chloroform/methanol/water=5/1). The identification of the compound was performed by IR and $^1$H-NMR, ESI-MS. A compound 21 (R$_f$=0.12, chloroform/methanol=10/1, silica gel plate), a compound 22 (R$_f$=0.03) and a compound 24 (R$_f$=0.03) were produced in substantially the same manner.

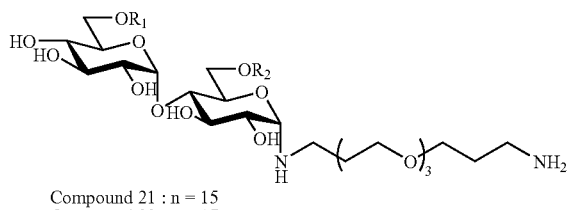

Compound 21 : n = 15
Compound 22 : n = 17

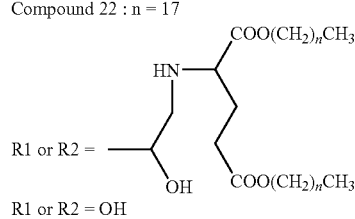

R1 or R2 =

R1 or R2 = OH

Compound 23 : n = 15
Compound 24: n = 17

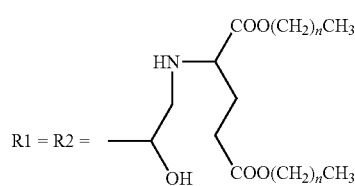

R1 = R2 =

Analysis results of the compound 23 (4C16):

Thin layer chromatography (silica gel plate, chloroform/methanol (10/1) (volume/volume): R$_f$: 0.09 (monospot).

Infrared absorption spectrum (cm$^{-1}$): 1738 ($v_{C=O}$, ester).

$^1$H-NMR (CD$_3$OD, 500 MHz, δ ppm): 0.89 (t, 12H, —CH$_3$); 1.28 (s, 104H, —CH$_2$—CH$_2$—); 1.61 (m, 8H, —CO—O—C—CH$_2$); 1.77 (m, 4H, glu β-CH$_2$, NH—C—CH$_2$—); 1.92 (m, 2H, CONH—C—CH$_2$—); 2.14 (m, 2H, glu β-CH$_2$); 2.24-2.41 (m, 8H, NH—CH$_2$—C(OH)—C—O—, NH—C—C(OH)—CH$_2$—O—); 2.44 (m, 4H, glu γ-CH$_2$); 2.68 (m, 2H, NH—C—CH(OH)—C—O—); 3.09 (m, 2H, NH—CH$_2$—); 3.15 (m, 2H, CONH—CH$_2$—); 3.49-3.79 (m, 12H, maltoseC-2,3,4,5,6); 3.63 (m, 14H, —O—CH$_2$—, glu α-CH); 4.06 (t, 2H, maltoseC-1); 4.15 (t, 4H, —CO—O—CH$_2$); 4.28 (t, 4H, —CO—O—CH$_2$).

2. Measurement of Critical Micelle Concentration of the Multi-Alkyl Chain-Type Glycolipid

[Method]

2 µL of a DPH solution (30 µM, THF) was added to a dispersion of glycolipid (compounds 21 through 24) (pure water 2 mL, 1, 5, 10, 20, 30, 50, 100 µM) and shaken at 37° C. for 2 hours. Fluorescence measurement was performed at 37° C. (DPH, $\lambda_{ex}$=357 nm, $\lambda_{em}$=430 nm), and the glycolipid concentration at which the fluorescence intensity rapidly increased was set as the critical micelle concentration (CMC).

[Results]

Figure 5:
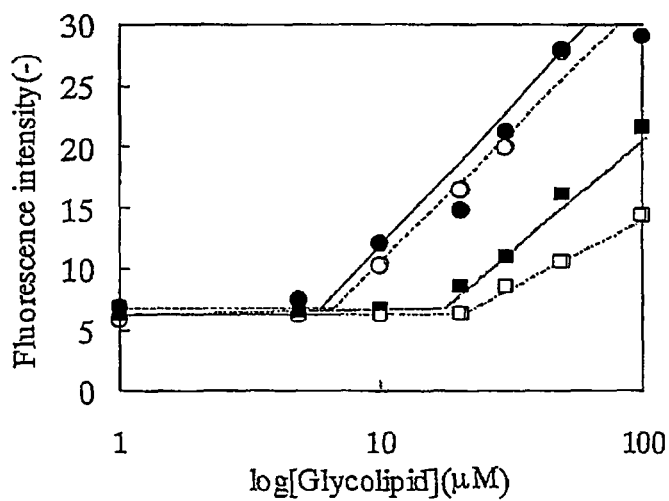
FIG. 5 is a graph showing CMC measurement results of glycolipid by different number of alkyl chains in glycolipid.

The CMC of the compound 21 was 20 µM, whereas the CMC of the compound 22 was 18 µM. The CMC was slightly decreased by changing the alkyl chain length from C16 to C18. By contrast, the CMC of the compound 23 was 8.0 µM and that of the compound 24 was 7.0 µM. It was recognized that the CMC was significantly decreased by increasing the number of alkyl chains from 2 to 4. Based on this, it was confirmed that an increase in the number of alkyl chains is effective to increase the hydrophobic interaction. FIG. 5 shows the results. The symbols in FIG. 5 represent the following: (□): 21 (2C16); (■): 22 (2C18); (○): 23 (4C16); and (●): 24 (4C18).

3. Preparation of Glycolipid-Introduced Liposome

DPPC (600 mg), cholesterol (316 mg) or glycolipid (compound 21 (3.9 mg), the compound 22 (4.1 mg), the compound 23 (6.0 mg), the compound 24 (6.4 mg)) (DPPC/cholesterol=1/1 (molar ratio), glycolipid=0.20 mol %) were dissolved in 30 mL of chloroform and mixed. Chloroform was removed by an evaporator, and the resultant substance was dried in vacuo and then hydrated while being stirred in 50 mL of PBS for 12 hours ([lipid]=2.0 g/dL). After the hydration, the resultant substance was annealed at 45° C. for 4 hours. By being formed into particles by an extruder (3000→800→650→450→300→220 nm×2), the particle diameter was controlled. The external aqueous phase was removed by centrifugation (10,000 rpm, 5 min.×3), and the resultant substance was re-dispersed in PBS to prepare a dispersion of glycolipid-introduced liposome.

4. Quantification of the Glycolipid on the Surface of the Liposome

100 µL of fluorescamine (30 mg/acetone 450 µL) was added to the liposome dispersion (PBS 1 mL, [Lipid]=0.15 g/dL) and stirred at room temperature for 30 minutes. Unreacted fluorescamine was removed by centrifugation (10,000 rpm, 5 min.×3), and the resultant substance was dissolved in chloroform/methanol=2/1 (total amount: 2 mL). The amino group on the surface of the liposome was quantified by fluorescence measurement ($\lambda_{ex}$=390 nm, $\lambda_{em}$=475 nm).

TABLE 4

Liposome characteristics and amount of NH$_2$ group on the liposome surface

| Glycolipid | Diameter (nm) | Outer NH$_2$ (mol %) | Ratio of outer NH$_2$ (%) | Outer NH$_2$ per liposome (×10$^2$) |
|---|---|---|---|---|
| 21 (2C16) | 280 ± 110 | 0.052 | 26 | 3.5 |
| 22 (2C18) | 290 ± 120 | 0.044 | 22 | 3.1 |
| 23 (4C16) | 270 ± 100 | 0.044 | 22 | 2.7 |
| 24 (4C18) | 280 ± 110 | 0.046 | 23 | 3.1 |

5. Introduction of Protein to the Surface of the Liposome

The NH$_2$ group introduced to the surface of the liposome and the NH$_2$ group on the surface of the protein were crosslinked by a disulfide bond using a crosslinker SPDP to bind 5 types of proteins each to the surface of the liposome (Table 5).

TABLE 5

Protein characteristics

| | Mw (kDa) | Isoelectric point (-) |
|---|---|---|
| α-lactalbumin (from bovie milk) | 14.0 | 4.1-4.8 |
| rHSA | 66.5 | 5.1 |
| Catalase (from bovie liver) | 232 | 5.5 |
| Ferritin (from equine spleen) | 440 | 4.0-5.0 |
| Thyroglobulin (from bovie thyroid) | 670 | 4.5 |

[Preparation of Protein]

8 μL (1.5 eq) of SPDP (3.8 mg/methanol 2 mL) was added to 2.0 g/dL of protein (1 mL, PBS) and stirred at room temperature for 30 minutes. Then, 200 μL (5 eq) of FITC (6 mg/1N NaOH 250 μL, PBS 750 μL) was added and stirred at room temperature for another 30 minutes. Unreacted SPDP and FITC were removed by gel column chromatography (Sephadex G25). 40 μL (20 mM) of DTT (15.4 mg/PBS 1 mL) was added and stirred for 30 minutes. Then, unreacted DTT was removed by gel column chromatography (Sephadex G25).

[Preparation of SPDP-Bound Liposome]

450 μL of SPDP (8 mg/methanol) was added to a dispersion of glycolipid-introduced liposome (PBS 10 mL [Lipid]=2.0 g/dL) and stirred at room temperature for 30 minutes. Unreacted SPDP was removed by centrifugation (10,000 rpm, 5 min.×3).

[Preparation of Protein-Bound Liposome]

1 mL of a solution of SPDP-introduced protein (0.4 g/dL) was added to a dispersion of SPDP-introduced liposome (PBS 4 mL [Lipid]=0.6 g/dL) and stirred at 4° C. for 12 hours. Unreacted protein was removed by centrifugation (10,000 rpm, 5 min.×3) to bind 5 types of protein each to the surface of the liposome.

[Quantification of the Binding Amount of Protein]

20 μL (20 mM) of DTT (15.4 mg/PBS 1 mL) was added to a dispersion of protein-bound liposome (PBS 1 mL [Lipid]=0.8 g/dL) and stirred at 37° C. for 4 hours. After performing centrifugation (10,000 rpm, 5 min.), fluorescence measurement (FITC, $\lambda_{ex}$=490 nm, $\lambda_{em}$=520 nm) on the supernatant (700 μL) was performed. The binding amount of the protein was quantified from the calibration curve (Table 6).

TABLE 6

Binding amount of protein

| | Mw (kDa) | Proteins per liposome (×10) | Binding efficiency (%) |
|---|---|---|---|
| α-lactalbumin | 14.0 | 18 | 55 |
| rHSA | 66.5 | 14 | 44 |
| Catalase | 232 | 10 | 30 |
| Ferritin | 440 | 9.2 | 28 |
| Thyroglobulin | 670 | 8.3 | 25 |

6. Measurement of the Release Rate of the Protein-Bound Glycolipid

The prepared liposome having each of 5 types of protein (FITC labeled) bound thereto was shaken at pH 7.4 at 37° C., and fluorescence measurement was performed on the release behavior of the protein-bound glycolipid.

[Method of Experiment]

Figure 6:
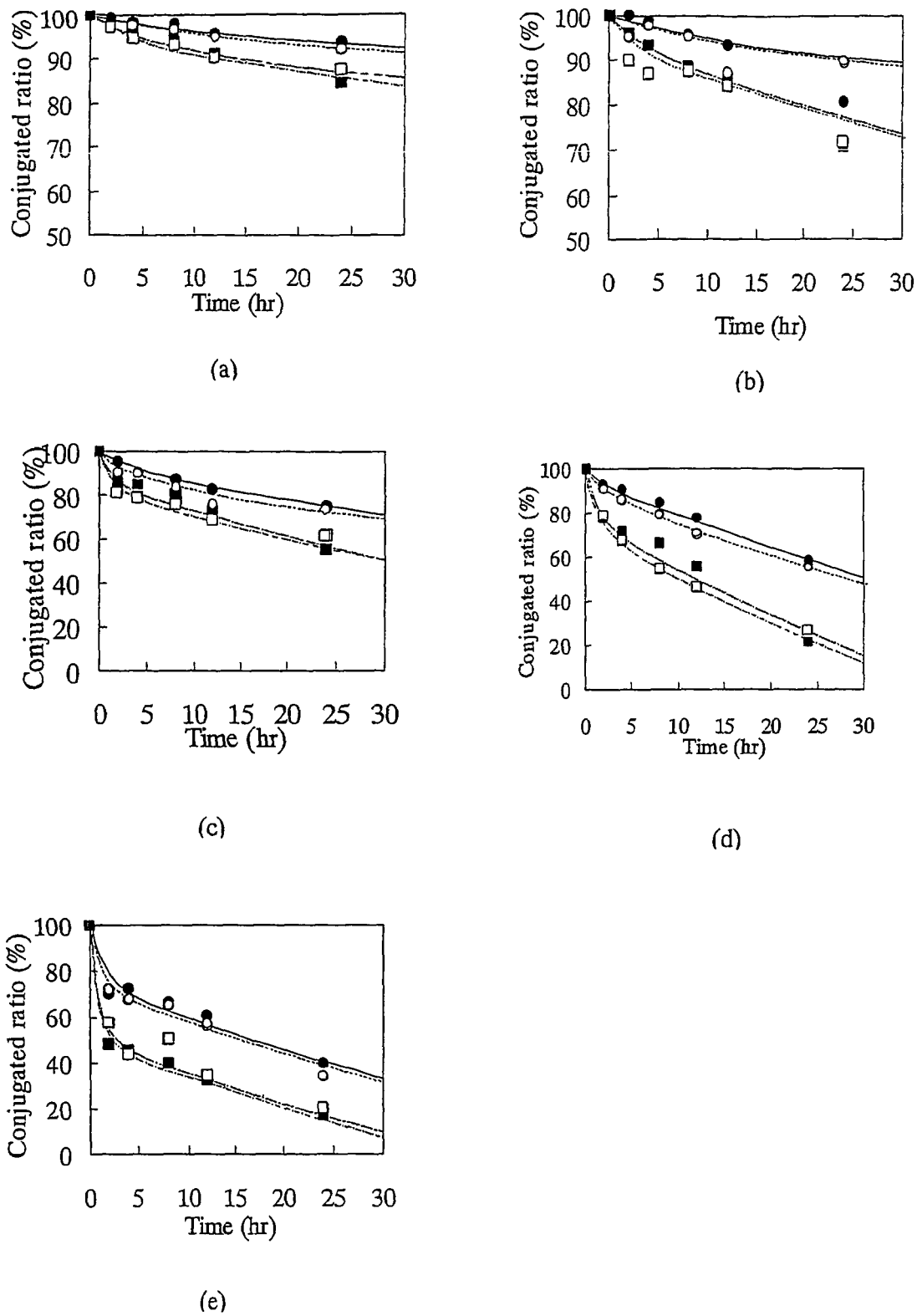
FIG. 6 is a graph for comparing the release rate of protein-bound membrane lipids from protein-bound liposomes by different types of protein.

A dispersion of protein-bound (or protein-conjugated) liposome (PBS 10 mL, [Lipid]=0.8 g/dL, stored at 4° C.) was shaken at 37° C. 5 minutes after the start, 1 mL of control (0 min) was sampled and subjected to centrifugation (10,000 rpm, 5 min.). Then, fluorescence measurement (FITC, $\lambda_{ex}$=490 nm, $\lambda_{em}$=520 nm) on the supernatant (700 μL) was performed, and the released protein-bound glycolipid was quantified based on the calibration curve. 2, 4, 8, 12 and 24 hours later also, the same operation was performed to measure the time-dependent change of the released protein. FIG. 6 shows the results. In FIG. 6, (a) shows the measurement results of α-lactalbumin (Mw: 14.0 kD); (b) shows the measurement results of r-HSA (Mw: 66.5 kD); (c) shows the measurement results of catalase (Mw: 232 kD); (d) shows the measurement results of ferritin (Mw: 440 kD); and (e) shows the measurement results of thyrogrobulin (Mw: 669 kD). The symbols in FIG. 6 represent the following: (□): 21 (2C16); (■): 22 (2C18); (○): 23 (4C16); and (●): 24 (4C18).

According to the measurement results of ferritin (Mw: 440 kDa), the release rate of the compound 21 was 12%/hr. whereas the release rate of the compound 22 was 11%/hr. The release rate was slightly suppressed by changing the alkyl chain length to C18. By contrast, the release rate of the compound 23 was 4.4%/hr. and that of the compound 24 was 3.5%/hr. The release rates of the compounds 23 and 24 were respectively 0.36 times and 0.32 times of those of the 2C (double chain) group. The release rate was significantly suppressed by increasing the number of alkyl chains from 2 to 4, and 2.3 times the amount of the protein was successfully retained 24 hours later. This difference in the release rate matches the difference in the CMC of the glycolipid. It is considered that the separation rate may be further suppressed by converting the hydroxyl group of the glycochain to an acetyl group to obtain a hydrophobic part and thus decreasing the CMC.

Figure 7:
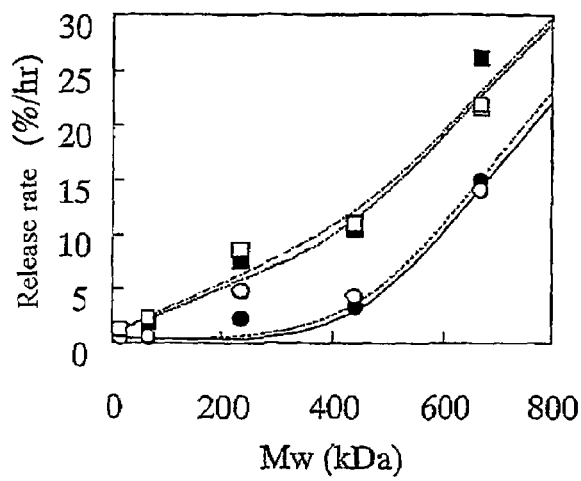
FIG. 7 is a graph for comparing the release rate of protein-bound glycolipids from protein-bound liposomes by different molecular weights of protein.

FIG. 7 shows the relationship between the molecular weight and the release rate of the protein. The symbols in FIG. 7 represent the following: (□): 21 (2C16); (■): 22 (2C18); (○): 23 (4C16); and (●): 24 (4C18). In the case of the double chain group, the molecular weight was increased 31 times (14 kDa to 440 kDa) while the release rate was increased 10.7 times (1.0%/hr. to 10.7%/hr.). By contrast, in the case of the quadruple chain group, the release rate was increased 5.0 times (0.7%/hr. to 3.9%/hr.). While the molecular weight of the protein was increased up to 440 kDa, the release rate was hardly accelerated. This indicates that in the case of the quadruple chain group, the suppressing effect on the release rate is increased as the molecular weight is increased up to 440 kDa. However, when the molecular weight is equal to or higher than 440 kDa, the protein is more easily released even with the quadruple chain group. It is considered that the influence by the difference in the number of alkyl chains decreases as the molecular weight increases.

Example 5

Synthesis of pH-Responsive Lipid

Z-Lys(H)-OBzl.benzenesulfonate (1.5 g, 2.8 mmol), BOP reagent (1.5 g, 3.4 mmol), lauric acid (380 mg, 3.4 mmol) and TEA (0.34 g, 3.4 mmol) were reacted in 30 mL distilled dichloromethane at 4° C. for 6 hours to form an amide bond. The resultant solution was separated with saturated sodium carbonate and water (chloroform phase was sampled), and the solvent was removed in vacuo. As a result, a pale yellow viscous liquid was obtained (2.01 g, yield: 91%). Then, the resultant compound was deprotected by a catalytic reduction method and purified with a column (silica gel, chloroform/methanol=(8/1) (volume/volume) to obtain a compound 25 as a pale yellow viscous liquid (596 mg, yield: 50%). The compound 25 (596 mg, 1.1 mmol), p-toluenesulfonic acid monohydrate (259 mg, 1.4 mmol) and n-tetradecanol (300 mg, 1.4 mmol) were refluxed in 100 mL of benzene at 105° C. for 12 hours to form an ester bond. The resultant solution was separated with a saturated aqueous solution of sodium carbonate and water (chloroform phase was sampled), and the solvent was removed in vacuo. Then, the resultant substance was recrystallized with methanol for purification to obtain a white solid 26 (550 mg, yield: 58%).

Compound 25

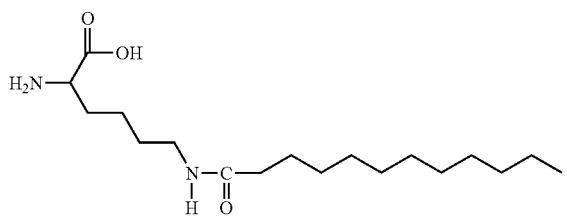

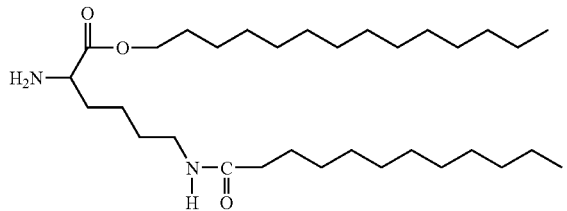

Compound 26

Analysis results of the compound 26:
Thin layer chromatography (silica gel, chloroform/methanol (8/1) (volume/volume): $R_f$: 0.50 (monospot).
$^1$H-NMR (CDCl$_3$, 500 MHz, δ (ppm)): 0.88 (t, 6H, —CH$_3$); 1.25 (m, 38H, —CH$_2$—, -Lys-β-γ-, CH$_2$—); 1.6 (m, 4H, —CO—O—CH$_2$—, —NH—CO—C—CH$_2$—); 2.2 (m, 2H, —CH$_2$—N—CO—); 3.6 (t, 1H, -Lys-); 4.0 (t, 4H, —COO—CH$_2$—, —N—CO—CH$_2$—); 4.9 (b, 1H, —N—H—C—O—).

The compound 26 (200 g, 0.38 mmol), BOP reagent (202 mg, 0.48 mmol), TEA (48 mg, 0.48 mmol) and Boc-Glu-O$^t$Bu (139 mg, 0.46 mmol) were reacted in 20 mL distilled dichloromethane for 12 hours to form an amide bond. The resultant solution was separated with saturated sodium carbonate and water (chloroform phase was sampled), and the solvent was removed in vacuo. The resultant substance was lyophilized to obtain a compound 27 (80 mg, 30%).

Compound 27

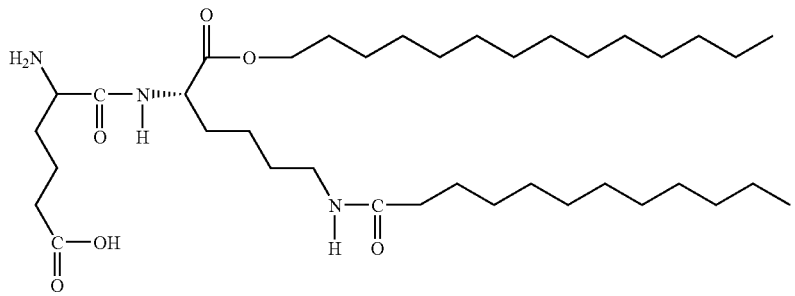

Analysis results of the compound 27:
Thin layer chromatography (silica gel, chloroform/methanol (8/1) (volume/volume): $R_f$: 0.71 (monospot).
$^1$H-NMR (CDCl$_3$, 500 MHz, δ(ppm)): 0.88 (t, 6H, —CH$_3$); 1.25 (m, 38H, —CH$_2$—, -Lys-β-γ-, CH$_2$—); 2.2 (m, 2H, —CH$_2$—N—CO—); 3.2 (t, 1H, -Lys-); 4.0 (t, 4H, —COO—CH$_2$—, —N—CO—CH$_2$—); 5.1 (b, 1H, —N—H—C—O—); 7.3 (s, 1H, -Glu-CO—NH—).

Compound 28 and 29 were synthesized as follows.
N-t-Boc-L-glutamic acid-g-butyl ester (764 mg, 2.52 mmol) and DCC (513 mg, 2.52 mmol) were dissolved in dichloromethane, stirred at 4° C. for 30 minutes, and then dropped to a dichloromethane solution having Glu2C16 (1 g, 1.68 mmol) dissolved therein. The reaction solution was stirred at room temperature for 5 hours and then filtered, and the solvent was removed in vacuo. The resultant substance was recrystallized with methanol at 4° C., filtered and dried to obtain a compound in which glutamic acid with a protected amino group and a protected carboxyl group is bound as a hydrophilic part to Glu2C16, as a white solid (1.15 g). This compound was dissolved in 10 mL of TFA and stirred at 4° C. for 2 hours. Then, chloroform was added thereto and washed twice with a saturated aqueous solution of sodium carbonate and twice with pure water. After the chloroform layer was dewatered with anhydrous sodium sulfate, the solvent was removed in vacuo. The resultant substance was dissolved in benzene and then lyophilized to obtain the compound 28 as a white solid (0.89 g).

The compound 29 was obtained by substantially in the same synthesis method as that of the compound 27 except that myristic acid was used instead of lauric acid.

3. Measurement of the Dispersion Stability of the Liposome

The stability of the prepared liposome was measured by particle measurement using light scattering. As a result, the particle diameter of the liposome was not changed by the membrane content of the compound 28 (Table 7).

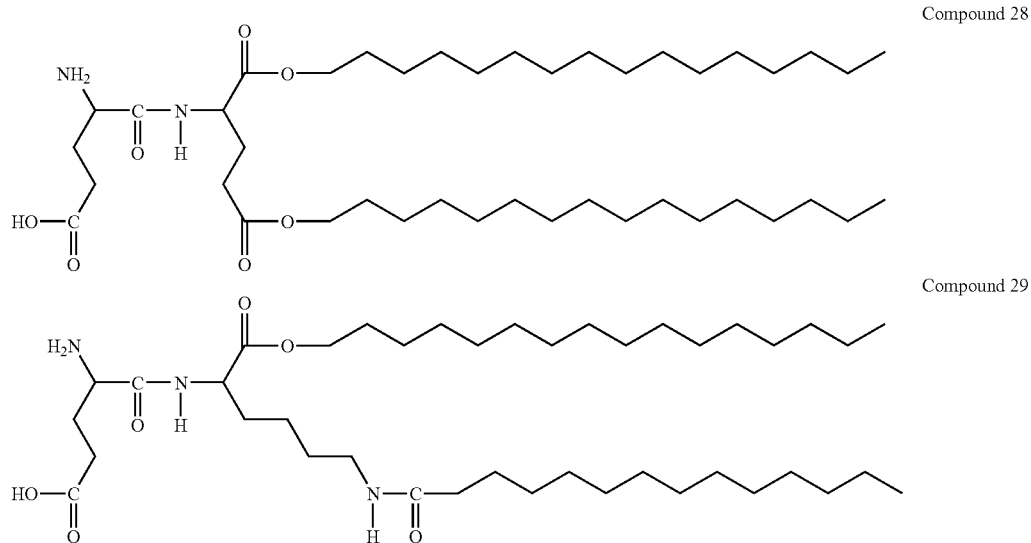

Compound 28

Compound 29

Analysis results of the compound 28:

Thin layer chromatography (silica gel, chloroform/methanol (4/1) (volume/volume): $R_f$: 0.24 (monospot).

$^1$H-NMR (CDCl$_3$, 500 MHz, δ (ppm)): 0.88 (t, 6H, —CH$_3$); 1.26 (m, 46H, —CH$_2$—CH$_2$—); 1.61 (m, 4H, —CO—O—CH$_2$—); 2.2 (m, 4H, glu β-CH$_2$—); 2.32, 2.41 (m, 4H, glu γ-CH$_2$—); 3.4 (m, 1H, —CH—CON—); 4.07, 4.12 (t, 4H, —CO—O—CH$_2$—); 4.51 (m, 1H, —CH—CO—O—).

Analysis results of the compound 29:

Thin layer chromatography (silica gel, chloroform/methanol (8/1) (volume/volume): $R_f$: 0.71 (monospot).

$^1$H-NMR (CDCl$_3$, 500 MHz, δ (ppm)): 0.88 (t, 6H, —CH$_3$); 1.25 (m, 38H, —CH$_2$—, -Lys-β-γ-, CH$_2$—); 2.2 (m, 2H, —CH$_2$—N—CO—); 3.2 (t, 1H, -Lys-); 4.0 (t, 4H, —COO—CH$_2$—, —N—CO—CH$_2$—); 5.1 (b, 1H, —N—H—C—O—); 7.3 (s, 1H, -Glu-CO—NH—).

2. Preparation of Liposome

A lipid mixture of 1,2-dioleoyl-sn-glycero-3-phosphocholine (DOPC, 29 mg, 36 mmol), cholesterol (18 mg, 48 mmol) and PEG-DSPE (2.1 mg, 0.036 mmol), and the compound 28 (26 mg, 36 mmol) were dissolved in 5 mL of t-butylalcohol and mixed, and then lyophilized. After being dried, the resultant substance was hydrated in phosphoric acid buffer saline (PBS) at room temperature for 12 hours such that the lipid concentration would be 2 wt. %, and extruded through pores down to a pore having a final diameter of 0.22 µm by an extrusion method. After the external aqueous phase was washed away with ultracentrifugation, the concentration of the resultant substance was adjusted based on the phospholipid quantification value to prepare a liposome having a particle diameter of about 250 nm.

TABLE 7

Characteristics of pH-responsive liposome

| Mixed lipid | Molar ratio | Particle diameter [nm] |
|---|---|---|
| DOPC/chol/(28)/PEG-DPE | 5/5/1/0.03 | 247 ± 101 |
| | 3/4/3/0.03 | 245 ± 98 |

4. Hydrolysis of the Compound 28 in the Liposome at Low pH

Figure 8:
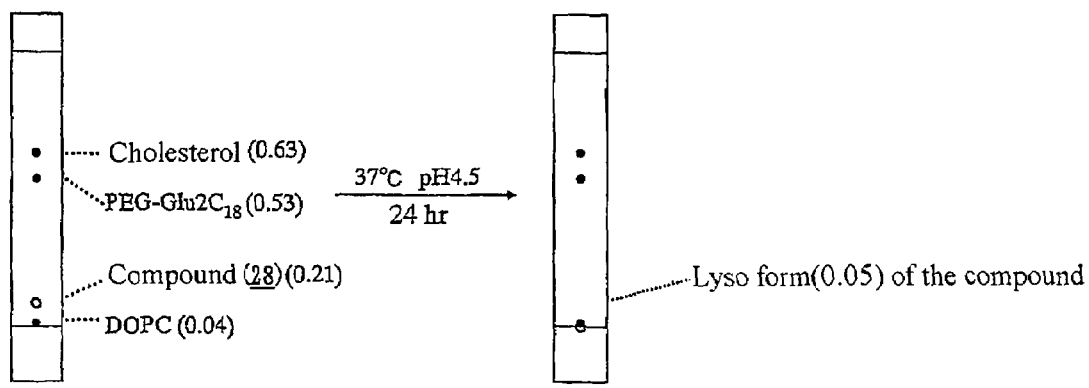
FIG. 8 shows thin layer chromatography detection results after hydrolysis in a pH-responsive liposome at low pH.

The prepared liposome (DOPC/chol/(28)/PEG-DPE=3/4/3/0.03, molar ratio) was dispersed in PBS of pH 4.5 at 37° C., and the dispersion was lyophilized 24 hours later. The dried mixed lipid powder was dissolved in chloroform and detected by thin layer chromatography (silica gel plate, chloroform/methanol (8/1) (volume/volume) detection: iodine). The detection results are shown in FIG. 8.

A spot of the compound 28 at $R_f$=0.21 disappeared and a new spot appeared in the vicinity of $R_f$=0.05. This is considered to have occurred because the compound 28 was hydrolyzed at pH 4.5 to generate a lyso form.

5. Promotion of Release of Encapsulated Molecules in the Liposome at Low pH

In order to investigate the pH responsiveness of the prepared liposome (DOPC/chol/(28)/PEG-DPE=3/4/3/0.03), a vesicle having cationic fluorescent HPTS (1-hydroxypyrene-3,6,8-trisulfonic acid) encapsulated in the molecules was prepared, and the leak of the fluorescent dye was measured. The measurement was performed ($\lambda_{ex}$: 413 nm, $\lambda_{em}$: 512 nm) after the prepared liposome was added to a 37° C. HEPES buffer solution at each of various pH values and the pH value was returned to pH 7.4 10 minutes later. The transmittance of the membrane (release ratio) was calculated from the following formula 1.1, utilizing the phenomenon that HPTS is quenched at high concentration and HPTS leaking from the vesicle emits fluorescence when being diluted.

$$\text{released \%} = (I_x - I_0)/(I_T \times 1.1 - I_0) \quad (1.1)$$

Figure 9:
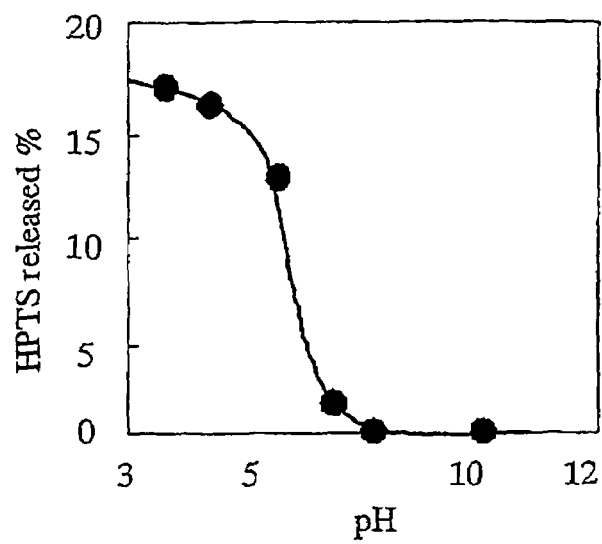
FIG. 9 is a graph showing the release behavior of fluorescent molecules encapsulated in a pH-responsive liposome in accordance with the pH value.
Figure 10:
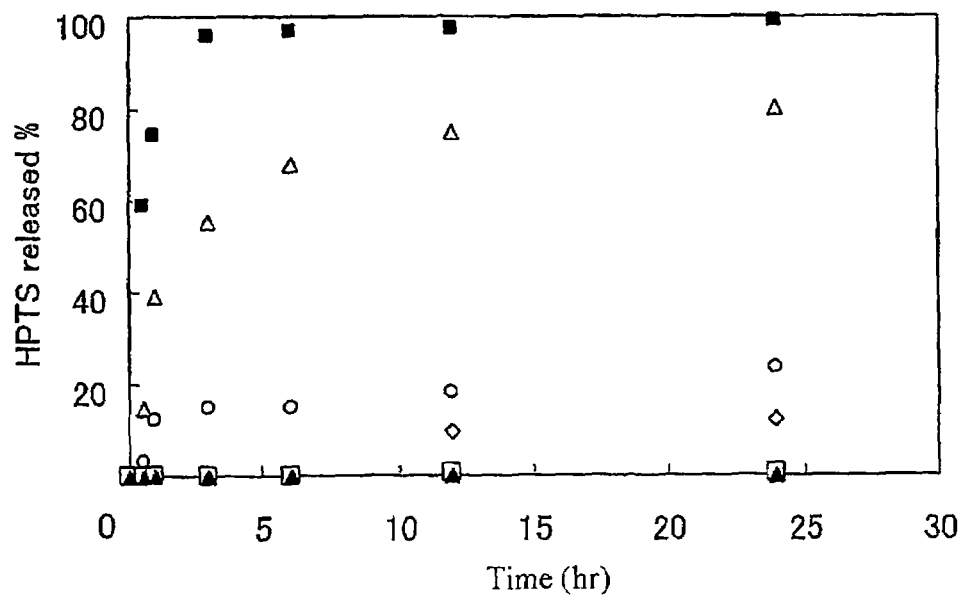
FIG. 10 is a graph showing the time-dependent release behavior of fluorescent molecules encapsulated in a pH-responsive liposome at various pH values.

$I_0$: fluorescence intensity at t=0(hr)
$I_x$: fluorescence intensity at t=x(hr)
$I_T$: fluorescence intensity when 300 μL of 10% Triton X is added FIG. 9 shows the release ratio at each pH value 10 minutes later. FIG. 10 shows the measurement results of time-dependent release of the encapsulated molecules at each pH value. The symbols in FIG. 10 represent the measurement results at the following pH values: (■): pH 3.5; (Δ): pH 4.5; (○): pH 5.5; (◇): pH 6.5; (□): pH 7.3; and (▲): pH 11. At pH 3.5, about 20% of the encapsulated fluorescence molecules was released, whereas at pH 6 or higher, the encapsulated fluorescence molecules were hardly released. It is considered that the following occurred. In the liposome having the compound 28 as a membrane component, the compound 28 was hydrolyzed at low pH. The lyso form of the hydrolyzed compound 28 had higher hydrophilicity and thus was released from the vesicle. Because of this, the molecule packing state of the bilayer was disturbed. As a result, the release rate of the encapsulated fluorescent molecules was increased.

A liposome having 10 mol % of each of the compounds 28 and 29 as a membrane component was prepared, and the pH responsiveness thereof was investigated.

The liposomes were prepared in substantially the same manner as described in "2. Preparation of liposome" above, and (DOPC/chol/(28 or 29)/PEG-DPE=5/5/1/0.03, molar ratio) was obtained. The characteristics thereof are shown in Table 7.

Figure 11:
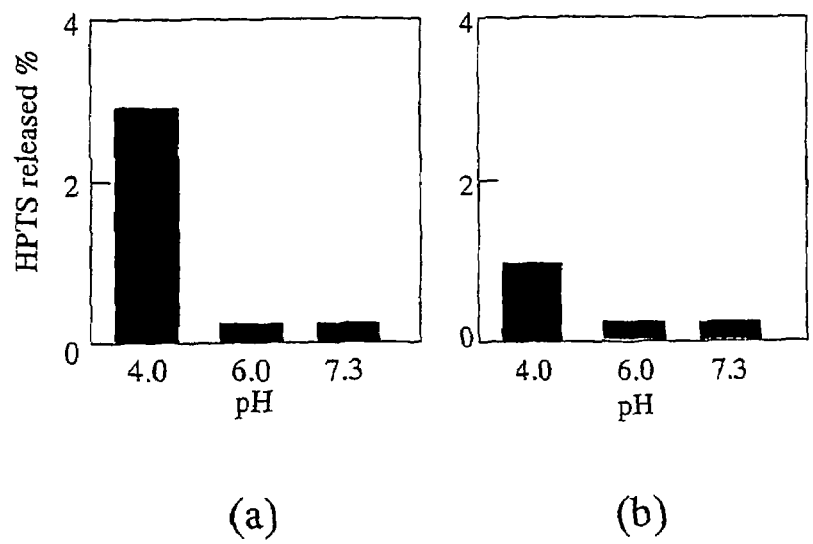
FIG. 11 is a graph showing the release behavior of fluorescent molecules encapsulated in a pH-responsive liposome in accordance with the pH value.

The release of the encapsulated molecules was calculated in substantially the same manner as described above. Namely, the fluorescence intensity was measured, and the release of the encapsulated molecules was calculated based on formula 1.1 above. The release ratio at each pH value 10 minutes later is shown in FIG. 11.

In the liposome having the compound 28 or 29 as a membrane component (10 mol %), the encapsulated molecules were rapidly released at pH 4. Because the release ratio increased at low pH, it is considered that the generated lyso form was released by hydrolysis of the decomposable lipid (compound 28 or 29), and at that point, the molecule packing state of the bilayer of the liposome was disturbed to accelerate the release of the encapsulated molecules.

Example 6

1. Synthesis of Disulfide Lipid

A disulfide lipid having a disulfide group in a hydrophobic part was synthesized in accordance with the following scheme.

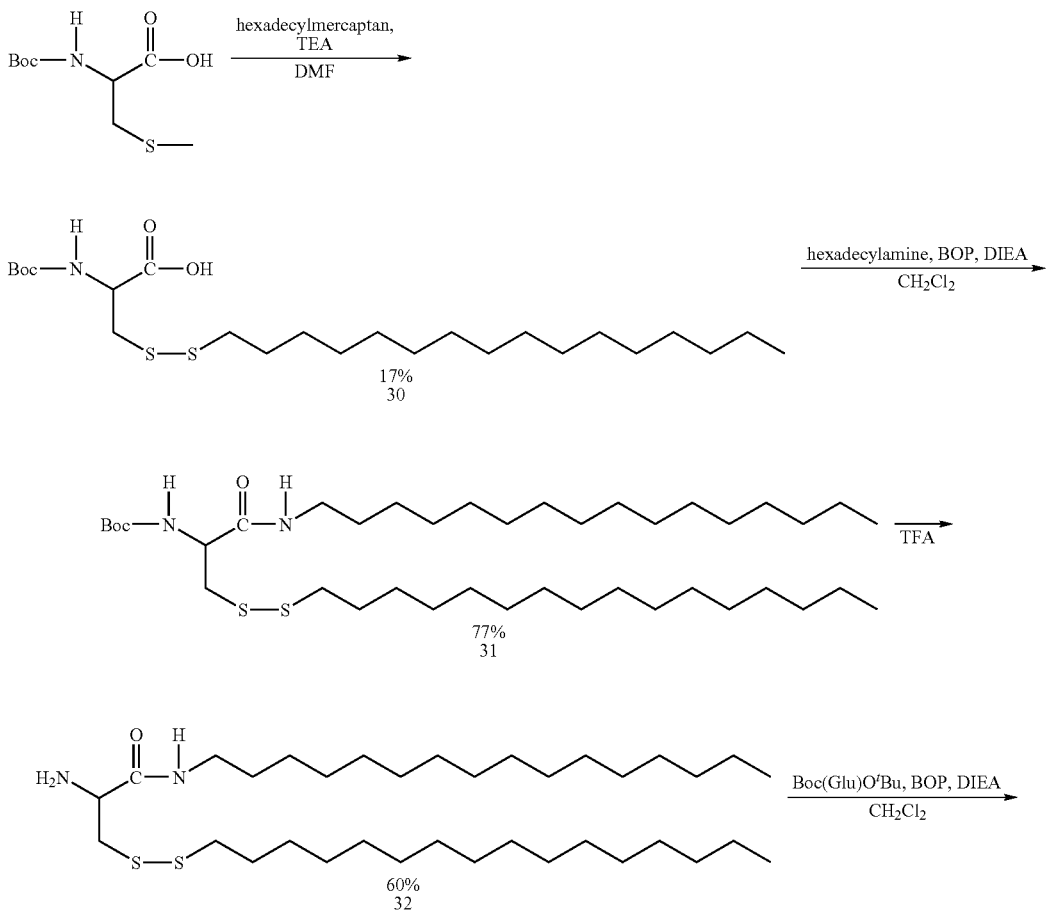

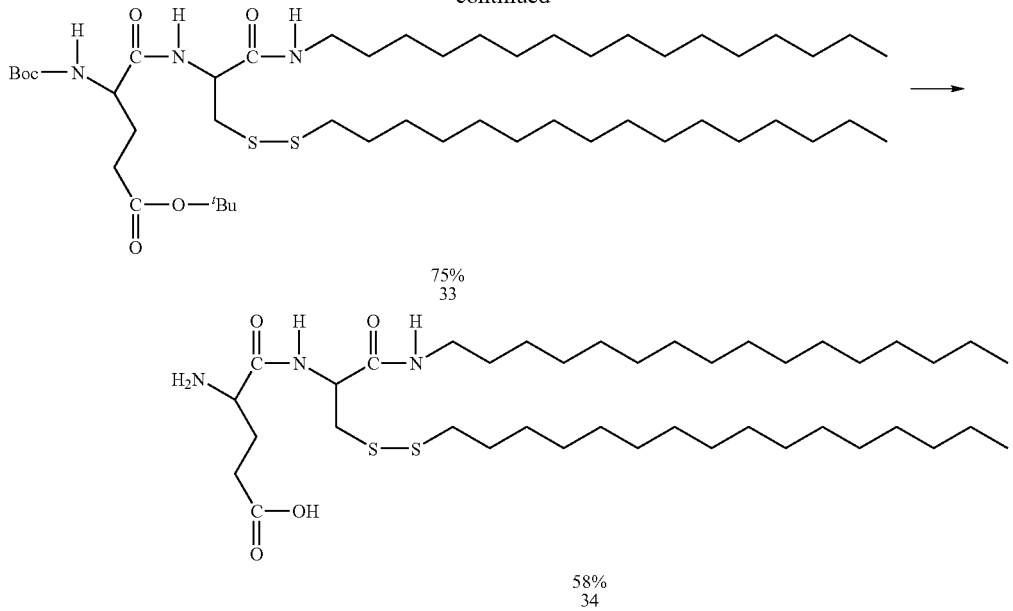

75%
33

58%
34

(A) Nα,Nα'-di-Boc-L-cystine ((Boc-Cys-OH)$_2$) (2.64 g, 6 mmol) was dissolved in 40 mL of DMF, and hexadecylmercaptan (1.55 g, 6 mmol) dissolved in TEA (7 mL, 50 mmol) was dropped thereto. The reaction was allowed at 40° C. for 2 hours to form a disulfide bond. After the solvent was removed, the resultant substance was dissolved in diethylether, and separated with saturated potassium hydrogen sulfate, saturated sodium hydrogen carbonate, and sodium chloride (diethylether layer was recovered). After the solvent was removed in vacuo, the resultant substance was purified with a column (neutral silica gel, chloroform/methanol=9/1 (volume/volume)) to obtain a compound 30 as a white solid (437 mg, yield: 16%).

Analysis results of the compound 30:
Thin layer chromatography (silica gel, chloroform/methanol (9/1) (volume/volume): R$_f$: 0.17 (monospot).

$^1$H-NMR (CDCl$_3$, 500 MHz, δ (ppm)): 0.85 (t, 3H, —CH$_3$), 1.23 (br, 26H, —CH$_2$—), 1.38 (s, 9H, Boc), 1.58 (m, 2H, S—CH$_2$—CH$_2$—), 2.69 (t, 2H, S—CH$_2$—), 2.93, 3.06 (dd, 1H, NH—CH(COOH)—CH$_2$—), 4.16 (t, 1H, NH—CH(COOH)—).

(B) The compound 30 (372 mg, 0.78 mmol) was dissolved in 20 mL of dichloromethane, and hexadecylamine (188 mg, 0.78 mmol), DIEA (0.33 mL, 0.85 mmol) and BOP reagent (442 mg, 1 mmol) were added thereto and reacted at room temperature for 2 hours to form an amide bond. After the reaction was completed, the resultant substance was dissolved in chloroform and separated with saturated potassium hydrogen sulfate, saturated sodium hydrogen carbonate, and sodium chloride (chloroform layer was recovered). After the solvent was removed in vacuo, the resultant substance was recrystallized with 60° C. methanol to obtain a compound 31 as a white powder (420 mg, yield: 77%).

Analysis results of the compound 31:
Thin layer chromatography (silica gel, chloroform/methanol (9/1) (volume/volume): R$_f$: 0.90 (monospot).

$^1$H-NMR (CDCl$_3$, 500 MHz, δ (ppm)): 0.88 (t, 6H, —CH$_3$), 1.25 (br, 52H, —CH$_2$—), 1.45 (s, 9H, Boc), 1.59 (m, 2H, NH—CH$_2$—CH$_2$—), 1.65 (m, 2H, S—CH$_2$—CH$_2$—), 2.71 (t, 2H, S—CH$_2$—), 3.02-3.04 (dd, 1H, NH—CH(COOH)—CH$_2$—), 3.24 (t, 2H, NH—CH$_2$—), 4.36 (t, 1H, NH—CH(COOH)—).

(C) The compound 31 (415 mg, 0.59 mmol) was dissolved in 20 mL of TFA, and the Boc group was deprotected at 4° C. for 1 hour. After the reaction was completed, the resultant solution was separated with saturated sodium hydrogen carbonate and water (chloroform layer was recovered). After the solvent was removed in vacuo, the resultant substance was purified with a column (neutral silica gel, chloroform/methanol=30/1 (volume/volume)) to obtain a compound 32 as a white powder (252 mg, yield: 71%).

Analysis results of the compound 32:
Thin layer chromatography (silica gel, chloroform/methanol (9/1) (volume/volume): R$_f$: 0.68 (monospot).

$^1$H-NMR (CDCl$_3$, 500 MHz, δ(ppm)): 0.88 (t, 6H, —CH$_3$), 1.25 (br, 52H, —CH$_2$—), 1.50 (m, 2H, NH—CH$_2$—CH$_2$—), 1.67 (m, 2H, S—CH$_2$—CH$_2$—), 2.70 (t, 2H, S—CH$_2$—), 3.23 (t, 2H—CONH—CH$_2$—), 3.29, 3.31 (dd, 1H, NH—CH(COOH)—CH$_2$—), 3.68 (t, 2H, NH—CH(COOH)—).

(D) The compound 32 (250 mg, 0.42 mmol) was dissolved in 15 mL of dichloromethane, and DIEA (0.45 mL, 1.2 mmol), Boc-Glu(O$^t$Bu)—OH (140 mg, 0.46 mol) and Boc reagent were reacted together with dichloromethane at room temperature for 10 hours to form an amide bond. After the reaction was completed, the resultant substance was dissolved in chloroform and separated with saturated potassium hydrogen sulfate, saturated sodium hydrogen carbonate and water (chloroform layer was recovered). After the solvent was removed in vacuo, the resultant substance was recrystallized with 60° C. methanol to obtain a compound 33 as a white powder (317 mg, yield: 85%).

Analysis results of the compound 33:
Thin layer chromatography (silica gel, chloroform/methanol (9/1) (volume/volume): R$_f$: 0.84 (monospot).

$^1$H-NMR (CDCl$_3$, 500 MHz, δ(ppm)):
0.87 (t, 6H, —CH$_3$), 1.25 (br, 52H, —CH$_2$—), 1.44, 1.46 (s, 18H, Boc), 1.52 (m, 2H, NH—CH$_2$—CH$_2$—), 1.66 (m, 2H, S—CH$_2$—CH$_2$—), 1.85, 2.17 (dd, 1H, —NH—CH (COOH)—CH₂—CH₂—), 2.33 (t, 2H, —CH₂—COO), 2.71 (t, 2H, —S—CH₂—), 3.07 (d, 2H, —CH₂—S—), 3.24 (t, 2H, CONH—CH₂—), 4.25 (t, 1H, Boc-NH—CH(COOH)—), 4.67 (t, 1H, —NH—CH(COOH)—).

(E) 10 mL of TFA was added to the compound 33 (117 mg, 0.13 mmol), and the Boc group and the O$^t$Bu group were deprotected at 4° C. for 2.5 hours. After the reaction was completed, the resultant solution was separated with saturated sodium carbonate and water (chloroform layer was recovered). The resultant substance was purified with a column (neutral silica gel, chloroform/methanol=9/1 (volume/volume)) to obtain a compound 34 (Glu-Cys-SC$_{16}$) as a white powder (65 mg, yield: 69%).

Analysis results of the compound 34:

Thin layer chromatography (silica gel, chloroform/methanol (4/1) (volume/volume): R$_f$: 0.11 (monospot).

$^1$H-NMR (CDCl₃, 500 MHz, δ(ppm)):

0.80 (t, 6H, —CH₃), 1.18 (br, 52H, —CH₂—), 1.42 (m, 2H, NH—CH₂—CH₂—), 1.58 (m, 2H, S—CH₂—CH₂—), 2.02, 2.09 (dd, 1H, —NH—CH(COOH)—CH₂—CH₂—), 2.40 (t, 2H, —CH₂—COO), 2.62 (t, 2H, —S—CH₂—), 2.85, 3.15 (dd, 2H, —CH₂—S—), 3.01 (t, 2H, CONH—CH₂—), 3.52 (t, 1H, NH₂—CH(COOH)—), 4.50 (t, 1H, —NH—CH(COOH)—).

2. Preparation of Liposome

DPPC, cholesterol, Glu-Cys-SC$_{16}$ and PEG-Glu2C$_{16}$ were mixed at a molar ratio of 3/4/3/0.03, and dissolved in chloroform containing a small amount of methanol such that the final concentration would be 5 wt. %. After the dissolution, the solvent was removed and the resultant substance was dried in vacuum to obtain a mixed lipid powder. In order to obtain a calcein-encapsulating liposome, the mixed lipid was hydrated (r.t., 6 hr.) in a 100 mM aqueous solution of calcein (2 wt. %), and then the particle diameter was controlled (φ=268±103 nm) by a high pressure extrusion method (filter pore diameter: 5000 nm, 650 nm, 450 nm, 220 nm×2). Unencapsulated calcein was removed by a Sephadex G-75 column.

The prepared calcein-encapsulating liposome (total lipid concentration: 1 mg/ml) was added to an aqueous solution of a reductant (cysteine or glutathione) having varied concentrations (final concentration: 10, 5, 1.0, 0.5, 0.1 mM) and shaken for 1 hour. Then, fluorescence measurement ($\lambda_{ex}$: 488 nm, $\lambda_{em}$: 517 nm) was performed at pH 4.7, and the calcein release ratio was calculated from the following formula.

Figure 12:
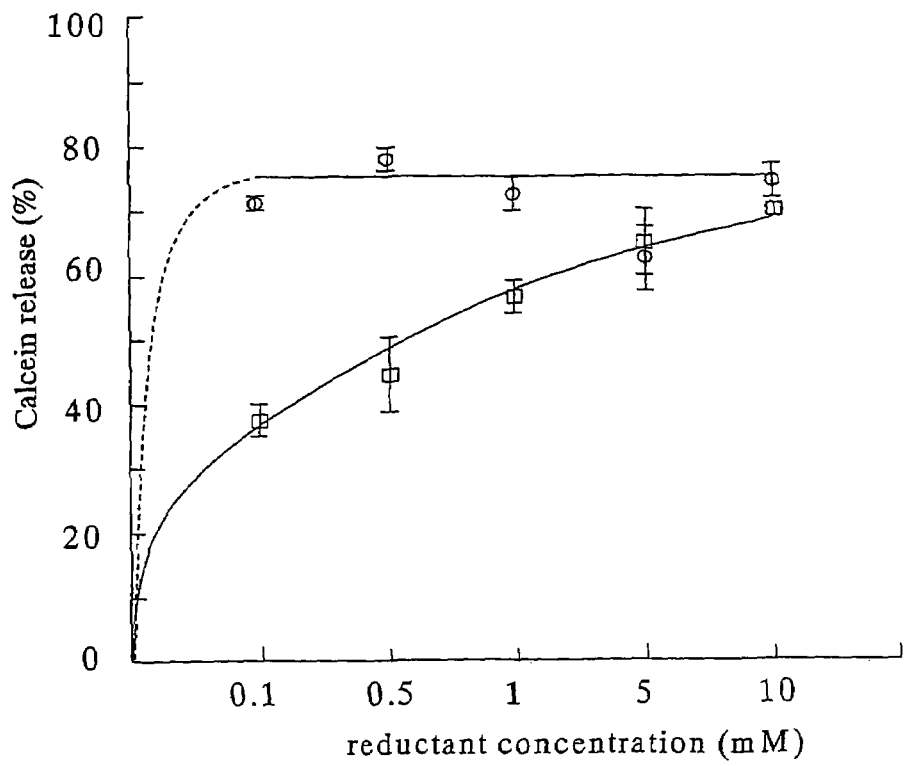
FIG. 12 is a graph showing the release behavior of calcein encapsulated in a liposome including disulfide lipid when a reductant is added.

Calcein release ratio (%)=$(F_x-F_0)/(F_{100}-F_0)\times 100$ $F_x$=fluorescence intensity after the reduction
$F_{100}$=fluorescence intensity after the liposome was entirely solubilized
$F_0$=fluorescence intensity after being left in PBS at 37° C. for 1 hour The results are shown in FIG. 12. In FIG. 12, -○- represents a system containing cysteine, and -□- represents a system containing glutathione. As shown in FIG. 12, with the liposome containing Glu-Cys-SC$_{16}$ as a membrane component, the release of calcein was accelerated due to the presence of the reductant. Especially with the system containing cysteine, the release ratio was high at each concentration. By contrast, with the system containing glutathione, the release ratio was increased depending on the concentration. This is considered to have occurred because cysteine had higher membrane permeability and higher reduction rate constant based on the vesicle membrane and thus allowed Glu-Cys-SC$_{16}$ to become lyso more rapidly, and the separation of the lyso form from the liposome membrane caused the encapsulated calcein to be released. It is considered that the reason why the release ratio of calcein was kept at 70% is that after Glu-Cys-SC$_{16}$ became lyso form and was released, the liposome retained calcein as a stable vesicle.

Example 7

1. Synthesis of Maltopentaose (MP)-Bound Lipid

A maltopentaose-bound lipid was synthesized in accordance with the following scheme.

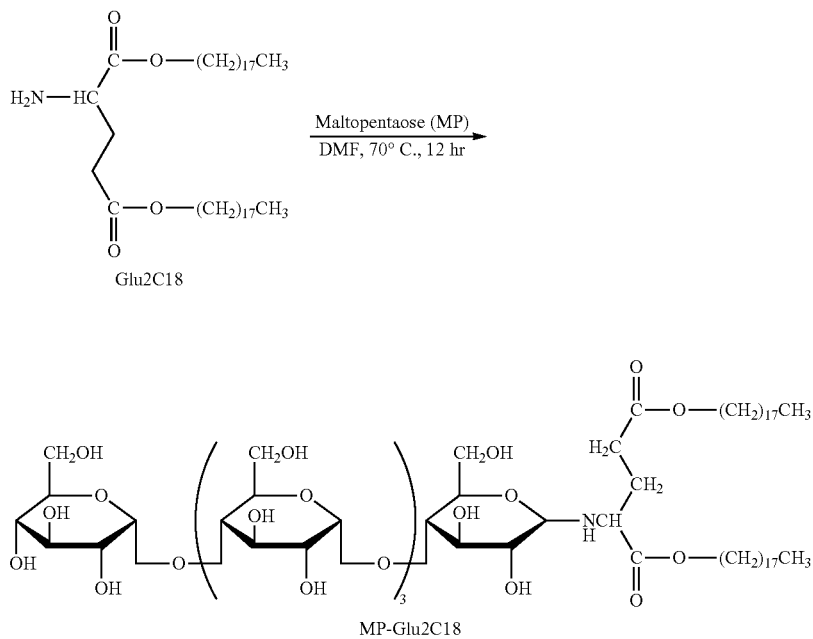

MP (0.25 g, 0.302 mmol) and Glu2C18 (0.098 g, 0.151 mmol) were dissolved in DMF (2 mL) and stirred at 70° C. for 12 hours. It was confirmed by ninhydrin that an amine spot of Glu2C18 disappeared, and the reaction solution was purified by reprecipitation with acetone and rinsing with water to obtain MP-Glu2C18 as a white powder (0.145 g, yield: 66%). Analysis results of MP-Glu2C18:

TLC (silica gel plate, chloroform/methanol/water (3/4/1) (v/v/v): $R_f$: 0.85 (monospot).

IR (cm$^{-1}$): 1736 [$v_{C=O}$(amide)]; 1676 [$v_{C=O}$(amide)]; 1553 [$\delta_{N-H}$(amide)].

$^1$H-NMR (DMSO-d$_6$, 500 MHz, $\delta$(ppm)): 0.8 (6H); 1.2 (60H); 1.5 (4H); 2.0 (2H); 2.3 (2H); 2.8-5.6 (56H); 7.9 (1H).

Figure 13:
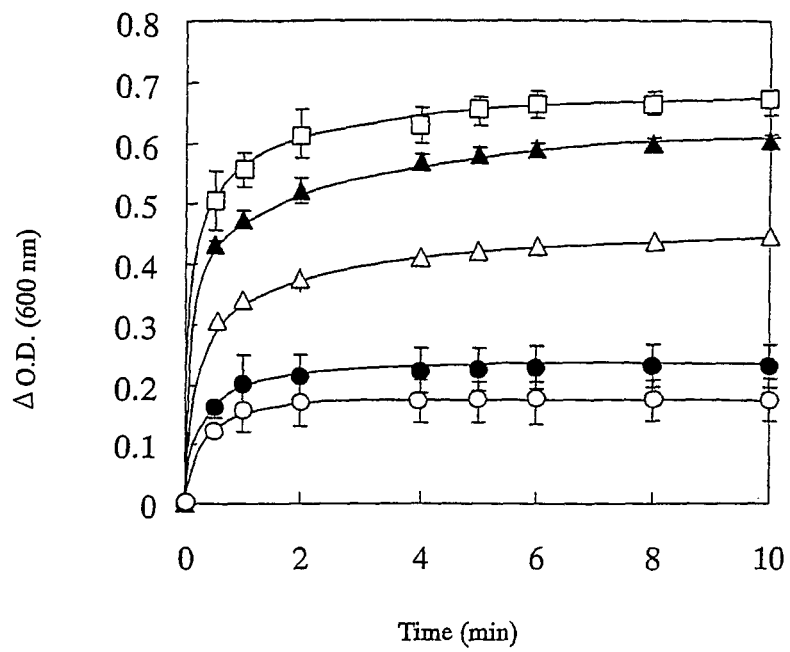
FIG. 13 is a graph showing the time-dependent change of the turbidity (O.P. value, $\lambda=600$ nm) of a liposome dispersion having various MP-Glu2C18 introduction ratios when a Con A solution is added to the liposome dispersion.
Figure 14:
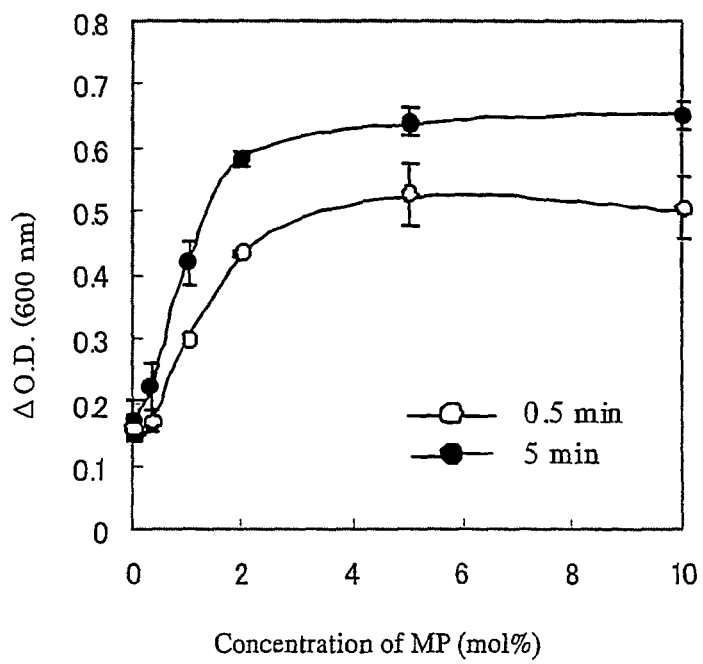
FIG. 14 is a graph showing the turbidity (O.P. value, $\lambda=600$ nm) change plotted in accordance with the MP-Glu2C18 introduction ratio, 0.5 minutes and 5 minutes after the state in FIG. 13.

2. Phenomenon that a Composite of MP-Introducing Liposome and Concanavalin (Con A) is Formed MP-Glu2C18 was introduced at 0, 0.3, 1, 2 and 10 mol % based on DPPC/cholesterol/DHSG=5/5/1 (molar ratio) to prepare a liposome solution (0.5 mg/ml) using 10 mM HEPES buffer (1 mM Ca$^{2+}$, pH 7.4). An aqueous solution (0.5 mg/ml) of lectin Con A having 4 recognition sites of D-glucose or D-mannose was added to the liposome solution, and the time-dependent change of the turbidity (O.P. value, $\lambda$=600 nm) of the aqueous solution was measured. FIG. 13 is a graph showing the time-dependent change of the turbidity (O.P. value, $\lambda$=600 nm) of the dispersion when a Con A solution was added to the liposome dispersion having various MP-Glu2C18 introduction ratios. The symbols in FIG. 13 represent the time-dependent change at the following MP-Glu2C18 introduction molar ratios: ○: 0 mol %; ●: 0.3 mol %; △: 1 mol %; ▲: 2 mol %; and □: 10 mol %. From immediately after the aqueous solution of Con A was added, an increase of the turbidity of the solution was observed. This is considered to have occurred because the added Con A recognized D-glucose at the terminus of the glycochain on the liposome surface and crosslinked the liposomes. FIG. 14 is a graph showing the turbidity (O.P. value, $\lambda$=600 nm) change plotted in accordance with the MP-Glu2C18 introduction ratio, 0.5 minutes and 5 minutes after the state in FIG. 13. In FIG. 14, ○ represents the turbidity change 0.5 minutes after FIG. 13 and ● represents the turbidity change 5 minutes after FIG. 13. It was observed that the turbidity increased depending on the MP-Glu2C18 introduction amount on the liposome surface, and the turbidity was rapidly increased when the introduction amount was 2 mol % or greater.

Figure 15:
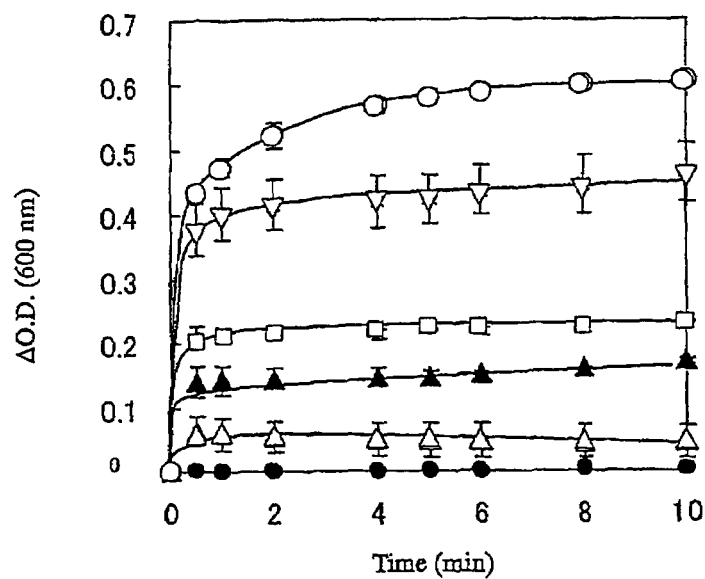
FIG. 15 is a graph showing the time-dependent change of the turbidity (O.P. value, $\lambda=600$ nm) of a liposome dispersion obtained when 2 mol % MP-Glu2C18-introduced liposome having 1 mol % PEG lipid (P125-2C14) introduced thereto is diluted at various dilution magnifications, and then a Con A solution is added thereto.

3. Phenomenon that the Composite of MP-Introduced Liposome and Concanavalin (Con A) is Dissociated 1 mol % PEG lipid (P125-2C14) was introduced to a 2 mol % MP-Glu2C18-introduced liposome, and the resultant system was diluted with varied dilution magnifications. To each resultant system, a Con A solution was added. FIG. 15 is a graph showing the time-dependent change of the turbidity (O.P. value, $\lambda$=600 nm) of the resultant dispersion. MPGlu2C18 was introduced at 2 mol % with respect to DPPC/cholesterol/DHSG=5/5/1 (molar ratio), and a liposome solution (0.5 mg/ml) was prepared using 10 mM HEPES buffer (1 mM Ca$^{2+}$, pH 7.4). To the liposome solution, an aqueous solution (0.5 mg/ml) of Con A was added. In this case, as shown in FIG. 15 with "○", the turbidity (O.P. value, $\lambda$=600 nm) of the aqueous solution was increased. It was found that when 5 mM EDTA was added thereto, as shown in FIG. 15 with "●", the turbidity increase was completely suppressed. This suggests that Ca$^{2+}$ is indispensable for Con A to recognize sugar.

Next, a 1 mol % PEG lipid (P125-2C14) solution was added to the external aqueous phase of the liposome dispersion to modify the liposome surface with the PEG chain, as shown in FIG. 15 with "△", the turbidity increase was suppressed. This means that the excluded volume effect of the PEG chain caused the recognition ability on MP on the liposome surface was disturbed and thus inhibited the functions. This system was diluted 20 folds (▲ in FIG. 15), 100 folds (□ in FIG. 15) and 200 folds (∇ in FIG. 15), and then the liposome was separated by ultracentrifugation and re-dispersed. When Con A was added in substantially the same manner to the resultant solution, a turbidity increase was observed as the dilution magnification was increased. This is considered to have occurred because the PEG lipid was separated from the masked liposome surface and thus the recognition ability of Con A on MP appeared.

Example 8

1. Preparation of H12-Vesicle 1,2-Distearoyl-sn-glycero-3-phosphatidylethanolamine (DSPE, 5 mg, 6.9 μmol) was dissolved in a chloroform/methanol mixed solvent (8/1 (v/v)), and triethylamine (10.4. μmol) was added thereto and stirred (r.t., 10 min). Further, N-(ε-maleimidocaproyl)succinimide ester (EMCS, 21.3 mg, 69 μmol) was added thereto and stirred (r.t., 1 hour). 1,2-Distearoyl-sn-glycero-3-phosphatidylcholine (DPPC, 253.2 mg, 350 μmol), cholesterol (106.5 mg, 280 μmol) and DHSG (48 mg, 69 μmol) were dissolved and dried to be thin film, and then the solvent was removed by vacuum drying. The resultant substance was hydrated with 15 mL of pure water while being stirred, and the particle diameter was controlled by an extrusion method (φ: 0.8, 0.6, 0.45, 0.22 μm). Unreacted EMCS and by-products were removed by centrifugation (100,000 g, 30 min.) to obtain maleimide group-introduced phospholipid vesicle (MAL-vesicle) (4 wt. %, 6 mL). Dodecapeptide having cysteine introduced at the N terminus beforehand (H12, 100 mM, 100 μL) was added to the MAL-vesicle and shaken (r.t., 12 hours). Unbound H12 was removed by centrifugation (100,000 g, 30 min.) to obtain H12-vesicle.

The binding amount of H12 on the surface of the vesicle was obtained by quantifying the unbound H12 with HPLC (TSK-GEL G3000PW$_{XL}$ column, 7.8 mm o.d.×300 min h., 1 mL/min., 36% (v/v) acetonitrile, 0.1% (v/v) trifluoroacetic acid) and counting backward.

2. Preparation of PEG-Introduced H12-Vesicle (PEG(H12)Vesicle)

An aqueous solution (17.0 μM, 15.8 mL) of PEG-bound lipid (P125-2C14) was mixed with an H12-vesicle dispersion of (17 mM, 5 mL) and stirred at 37° C. for 2 hours. Unintroduced PEG lipid was removed by ultracentrifugation (33,000 rpm, 30 min.) to obtain a PEG lipid-introduced vesicle (PEG (H12)vesicle).

3. Specific Binding of H12-Vesicle to Activated Platelet and Suppression on the Binding by PEG Chain Modification (Flow Cytometry)

[Method]

A sample labeled with $DiOC_{18}$ (vesicle, PEG-vesicle, H12-vesicle, PEG(H12)-vesicle, f.c. [lipid]=0.5 mg/mL) was mixed with washed human platelet ($1.0 \times 10^5/\mu L$, 50 μL). The platelet was activated with thrombin (f.c. 3 U/mL), shaken at 37° C. for 10 minutes, and immobilized with formaldehyde (f.c. 1% (v/v)). Based on the fluorescence positive ratio of platelet fraction, the binding ratio of H12-vesicle to platelet was observed.

[Results]

Figure 16:
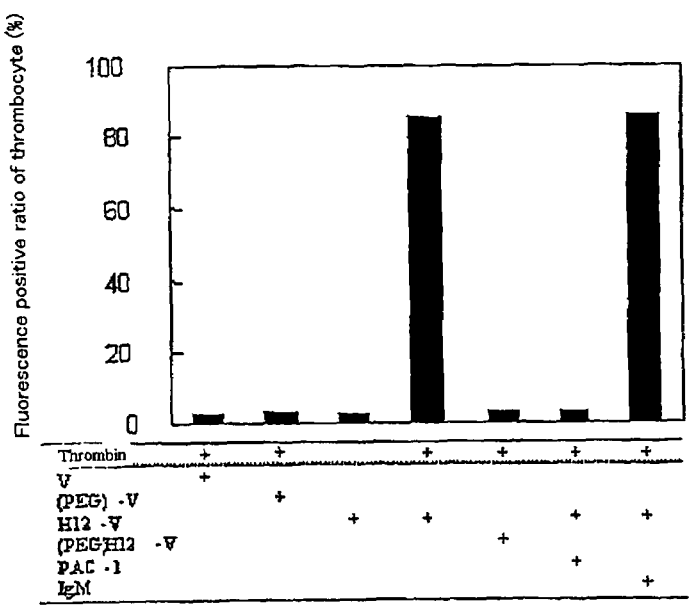
FIG. 16 is a graph showing that H12-vesicle is specifically bound to activated platelet and that the binding is suppressed by introduction of PEG to H12-vesicle.

FIG. 16 shows the results. In the presence of $DiOC_{18}$-labeled H12-vesicle, the fluorescence positive ratio of the activated platelet stimulated with thrombin was measured by a flow cytometry. The ratio was 85.6%, and H12-vesicle was confirmed to bind to activated platelet. Without stimulation with thrombin (2.1%), in the presence of PAC-1 (antibody inhibiting the binding of H12 to GPIIb/IIIa on the activated platelet) (3.1%), the binding was suppressed, as well as in the presence of vesicle (2.3%). Thus, it was clarified that H12-vesicle specifically binds to activated platelet.

The same experiment was performed using PEG(H12)-V with post-introduced PEG, the binding ratio to the activated platelet was decreased to 3.4%. This is considered to have occurred because the excluded volume effect of the PEG inhibited the functions of H12.

4. Binding of PEG(H12)-Vesicle to the Activated Platelet Because of the Separation of PEG Lipid (Flow Cytometry)

[Method]

A dispersion of PEG(H12)-vesicle was diluted 0, 6, 300 folds with PBS and shaken (r.t., 1 hour). The resultant substance was concentrated by centrifugation (100,000 g, 30 min.) to obtain 3 types of PEG(H12)-vesicle ([lipid]=3 mg/mL) with varied dilution magnifications.

Each type of PEG(H12)-vesicle (f.c. [lipid]=0.5 mg/mL) labeled with $DiOC_{18}$ was mixed with washed platelets ($1.0 \times 10^5/\mu L$, 50 μL). The resultant platelets were activated with thrombin (f.c. 3 U/mL), shaken at 37° C. for 10 minutes, and immobilized with formaldehyde (f.c. 1% (v/v)). As the positive control group, samples having PEG-unintroduced H12-vesicle were used, and as the negative control group, samples having vesicle were used. Based on the fluorescence positive ratio of platelet fractionation, the binding ratio of PEG(H12)-vesicle to platelet was observed. The results are shown in FIG. 17.

[Results]

Figure 17:
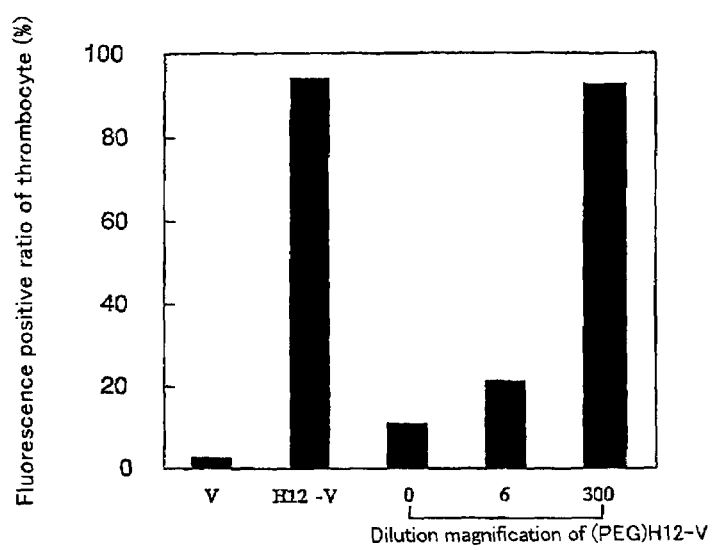
FIG. 17 is a graph for comparing the binding ratios of PEG(H12)-vesicle to activated platelet due to the release of PEG.

The binding ratio of PEG(H12)-vesicle (PEG(H12)-vesicle in FIG. 17) to the activated platelet was 11.0%. As the dilution magnification of PEG(H12)-vesicle increased, the binding ratio increased. When the dilution magnification was 300 times or higher, the binding ratio of PEG(H12)-vesicle was almost equivalent to that of H12-vesicle. From these results, it is considered that the release of the PEG-bound lipid was accelerated by dilution and the functions of H12 appeared.

INDUSTRIAL APPLICABILITY

A drug carrier according to the present invention can control the pharmacokinetics by an external environmental change and therefore is very useful as a preparation for preventing or treating various diseases.

The invention claimed is:

1. A drug carrier comprising a molecular assembly including therein amphiphilic molecules represented by: (drug)-(binding site A)-(hydrophilic part)-(binding site B)-(hydrophobic part), wherein binding site A is a site for binding the hydrophilic part and the drug;

the hydrophilic part is selected from the group consisting of polyethylene glycol and derivatives thereof; and the (binding site B)-(hydrophobic part) has a formula selected from the group consisting of formula [II] and [III]:

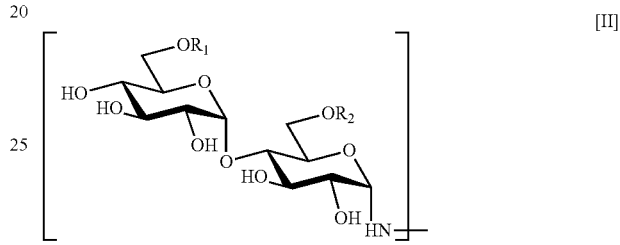

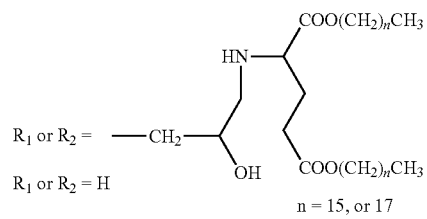

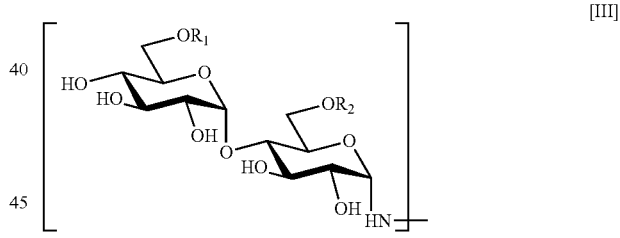

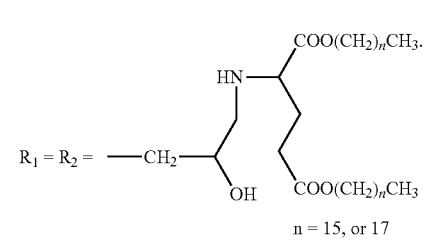

2. A drug carrier comprising a molecular assembly including therein amphiphilic molecules represented by: (drug)-(binding site A)-(hydrophilic part)-(binding site B)-(hydrophobic part)-(binding site B)-(hydrophilic pan), wherein binding site A is a site for binding the drug and the hydrophilic pan;

the hydrophilic part is selected from the group consisting of polyethylene glycol and derivatives thereof; and the (binding site B)-(hydrophobic part)-(binding site B) has the formula [IV]

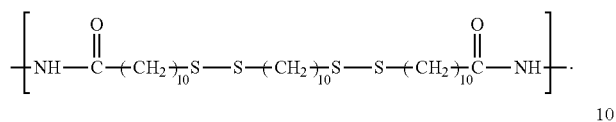

[IV]

3. A drug carrier comprising a molecular assembly including therein amphiphilic molecules represented by: (drug)-(binding site A)-(hydrophilic part)-(binding site B)-(hydrophobic part)-(binding site B)-(hydrophilic part)-(binding site A)-(drug), wherein binding site A is a site for binding the drug and the hydrophilic part;

the hydrophilic part is selected from the group consisting of polyethylene glycol and derivatives thereof; and the (binding site B)-(hydrophobic part)-(binding site B) has the formula [IV]

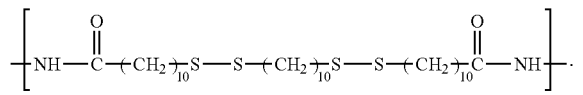

[IV]

\* \* \* \* \*